United States Patent
Abrams

(10) Patent No.: US 7,836,885 B2
(45) Date of Patent: *Nov. 23, 2010

(54) SEMI-AUTOMATIC EMERGENCY MEDICATION DOSE NEBULIZER

(76) Inventor: Robert Abrams, 152 Connetquot Dr., Oakdale, NY (US) 11769

(*) Notice: Subject to any disclaimer, the term of this patent is extended or adjusted under 35 U.S.C. 154(b) by 341 days.

This patent is subject to a terminal disclaimer.

(21) Appl. No.: 12/217,406

(22) Filed: Jul. 3, 2008

(65) Prior Publication Data

US 2009/0071473 A1 Mar. 19, 2009

Related U.S. Application Data

(63) Continuation-in-part of application No. 11/901,628, filed on Sep. 18, 2007.

(51) Int. Cl.
  *A61M 16/00* (2006.01)
  *A61M 16/14* (2006.01)
  *A61M 16/18* (2006.01)
(52) U.S. Cl. .............. 128/203.21; 128/200.14; 128/200.21; 128/203.12; 128/203.13; 128/203.27; 239/338; 239/370
(58) Field of Classification Search ............ 128/203.21, 128/200.14, 200.21, 203.12, 203.13, 203.27, 128/207.14; 239/338, 370
See application file for complete search history.

(56) References Cited

U.S. PATENT DOCUMENTS

| | | | |
|---|---|---|---|
| 0,322,105 A | 7/1885 | Istel | |
| 1,136,182 A * | 4/1915 | Swift | 30/113 |
| 2,515,020 A | 7/1950 | Scott | |
| 2,655,767 A | 10/1953 | Wenner | |
| 3,109,576 A | 11/1963 | Karl | |
| 3,380,636 A | 4/1968 | Ushkow et al. | |
| 3,831,606 A | 8/1974 | Damani | |
| 3,842,833 A * | 10/1974 | Ogle | 128/200.18 |
| 3,865,106 A | 2/1975 | Palush | |

(Continued)

FOREIGN PATENT DOCUMENTS

EP  0 385 156 A1  5/1990

(Continued)

OTHER PUBLICATIONS

"SPIRIVA HandiHaler", one page advertisement, 2002, author is "spiriva.com".

(Continued)

*Primary Examiner*—Kevin C Sirmons
*Assistant Examiner*—Clinton Ostrup
(74) *Attorney, Agent, or Firm*—Alfred M. Walker

(57) ABSTRACT

A conventional respiratory nebulizer has an emergency medication dose storage system conveniently useable in an emergency to deliver the stored medication dose directly to the nebulizing chamber quickly, reliably, and with a single impulse of manual force to a simple mechanical delivery system, thereby making the nebulizer useable in two steps: (a) opening the medication capsule with a simple opening action; and (b) inhaling the nebulized medication. The nebulizer can be operated without disassembling the nebulizer housing so as to expose the nebulizing chamber and without manually opening the liquid medication container and, without spillage and without manual pouring of the liquid medication directly into the nebulizing chamber, and without reassembling the nebulizer housing before positioning the inhaler mouthpiece in the mouth so as to inhale the nebulized medication.

11 Claims, 15 Drawing Sheets

U.S. PATENT DOCUMENTS

| | | | |
|---|---|---|---|
| 3,874,146 A | 4/1975 | Watkins | |
| 3,910,144 A | 10/1975 | Hess | |
| 3,945,378 A | 3/1976 | Paluch | |
| 3,971,377 A | 7/1976 | Damani | |
| 4,117,844 A * | 10/1978 | James | 128/203.15 |
| 4,159,568 A | 7/1979 | Berner | |
| 4,257,415 A | 3/1981 | Rubin | |
| 4,296,881 A | 10/1981 | Lee | |
| 4,465,474 A | 8/1984 | Mardorf et al. | |
| 4,508,250 A | 4/1985 | Punchak | |
| 4,515,063 A | 5/1985 | Lee | |
| 4,557,103 A | 12/1985 | Schwartz et al. | |
| 4,805,609 A | 2/1989 | Roberts | |
| 5,022,587 A | 6/1991 | Hochstein | |
| 5,152,284 A | 10/1992 | Valentini et al. | |
| 5,271,543 A | 12/1993 | Grant et al. | |
| 5,299,565 A | 4/1994 | Brown | |
| 5,388,571 A * | 2/1995 | Roberts et al. | 128/203.12 |
| 5,415,161 A * | 5/1995 | Ryder | 128/200.23 |
| 5,451,569 A | 9/1995 | Wong et al. | |
| 5,573,774 A | 11/1996 | Keenan | |
| 5,752,502 A | 5/1998 | King | |
| 5,894,841 A | 4/1999 | Voges | |
| 6,092,522 A * | 7/2000 | Calvert et al. | 128/203.21 |
| 6,196,218 B1 | 3/2001 | Voges | |
| 6,221,046 B1 | 4/2001 | Burroughs et al. | |
| 6,443,146 B1 | 9/2002 | Voges | |
| 6,443,152 B1 * | 9/2002 | Lockhart et al. | 128/203.21 |
| 6,470,884 B2 | 10/2002 | Horlin | |
| 6,543,443 B1 * | 4/2003 | Klimowicz et al. | 128/200.23 |
| 6,679,255 B2 | 1/2004 | Pera | |
| 6,705,316 B2 | 3/2004 | Blythe | |
| 6,747,058 B1 | 6/2004 | Dedhiya et al. | |
| 6,805,118 B2 | 10/2004 | Brooker et al. | |
| 6,851,626 B2 * | 2/2005 | Patel et al. | 239/338 |
| 6,889,687 B1 | 5/2005 | Olsson | |
| 6,966,166 B2 | 11/2005 | Kissling | |
| 6,981,499 B2 | 1/2006 | Anderson et al. | |
| 7,028,686 B2 | 4/2006 | Gonda et al. | |
| 7,343,915 B2 | 3/2008 | Addington et al. | |
| 7,388,076 B2 | 6/2008 | Sanberg et al. | |
| 7,418,785 B2 * | 9/2008 | Whitemiller et al. | 30/182 |
| 7,461,653 B2 | 12/2008 | Oliva | |
| 2002/0129812 A1 * | 9/2002 | Litherland et al. | 128/200.14 |
| 2002/0134372 A1 * | 9/2002 | Loeffler et al. | 128/200.14 |
| 2003/0140920 A1 * | 7/2003 | Chaudry et al. | 128/200.14 |
| 2004/0094146 A1 | 5/2004 | Schiewe et al. | |
| 2005/0178382 A1 | 8/2005 | Riley et al. | |
| 2006/0060194 A1 | 3/2006 | Oliva | |
| 2006/0102175 A1 | 5/2006 | Nelson | |
| 2007/0063072 A1 | 3/2007 | Calvo et al. | |
| 2007/0163572 A1 | 7/2007 | Addington et al. | |

FOREIGN PATENT DOCUMENTS

| | | | |
|---|---|---|---|
| WO | WO 8902289 A1 * | 3/1989 | |
| WO | PCT/US2008/010780 A1 | 10/2009 | |
| WO | PCT/US2009/001634 A1 | 10/2009 | |

OTHER PUBLICATIONS

Bertron, Kim, "Simple Shot Syringe", johnmuirhealth.com/lt, 10 page website, May 17, 2007.

* cited by examiner

To Compressor

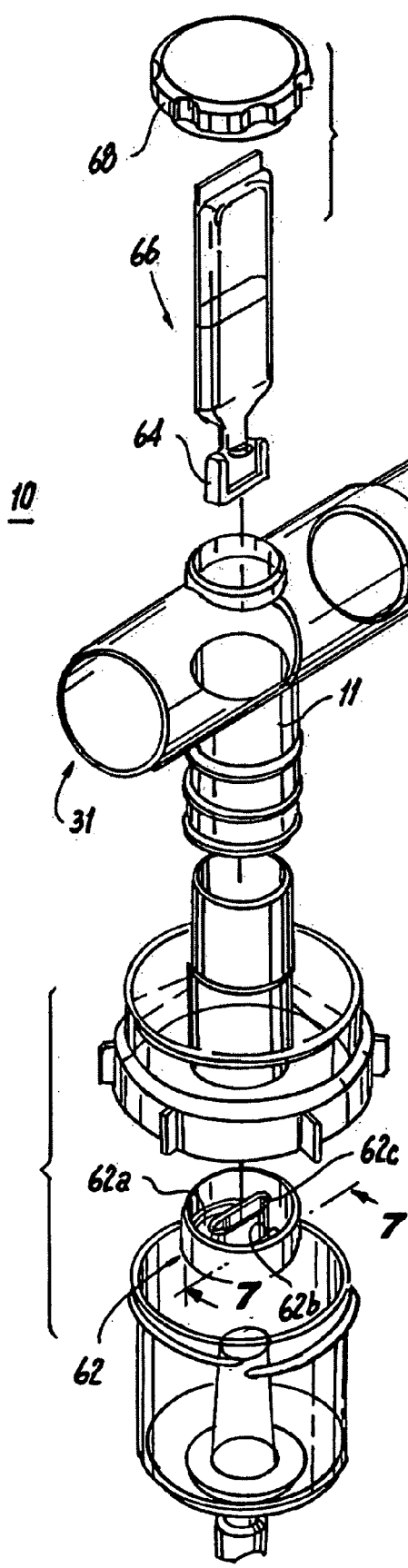
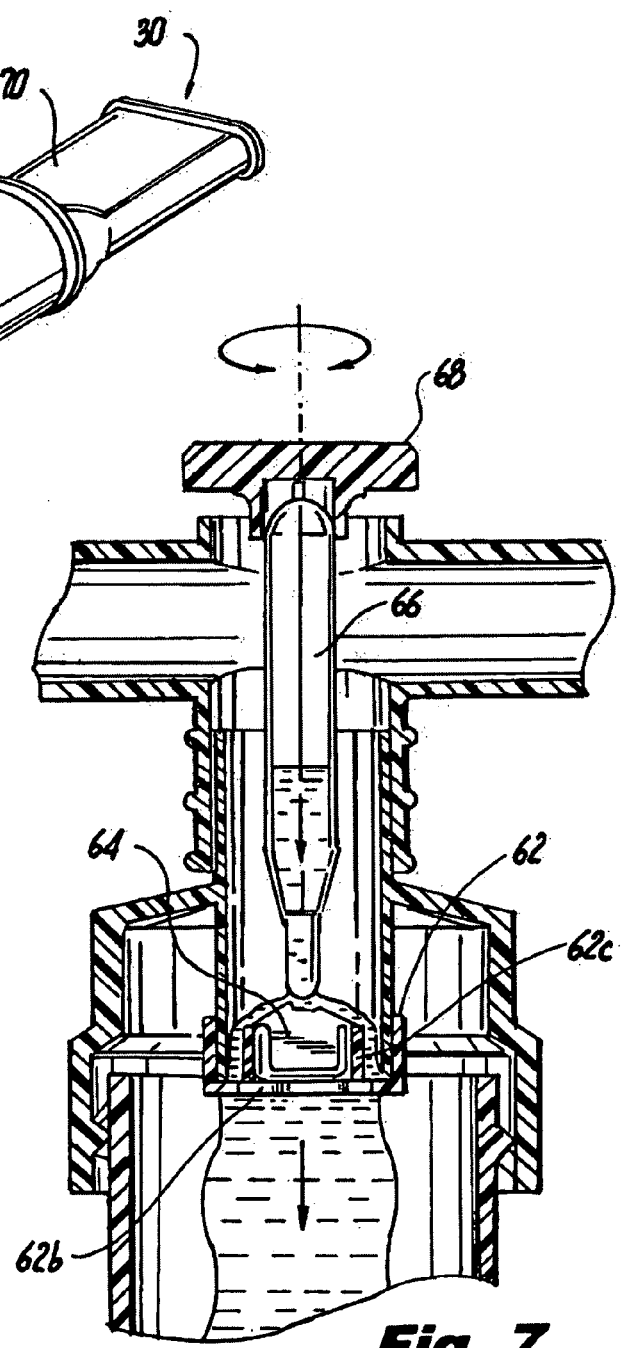
Fig. 6
Fig. 7

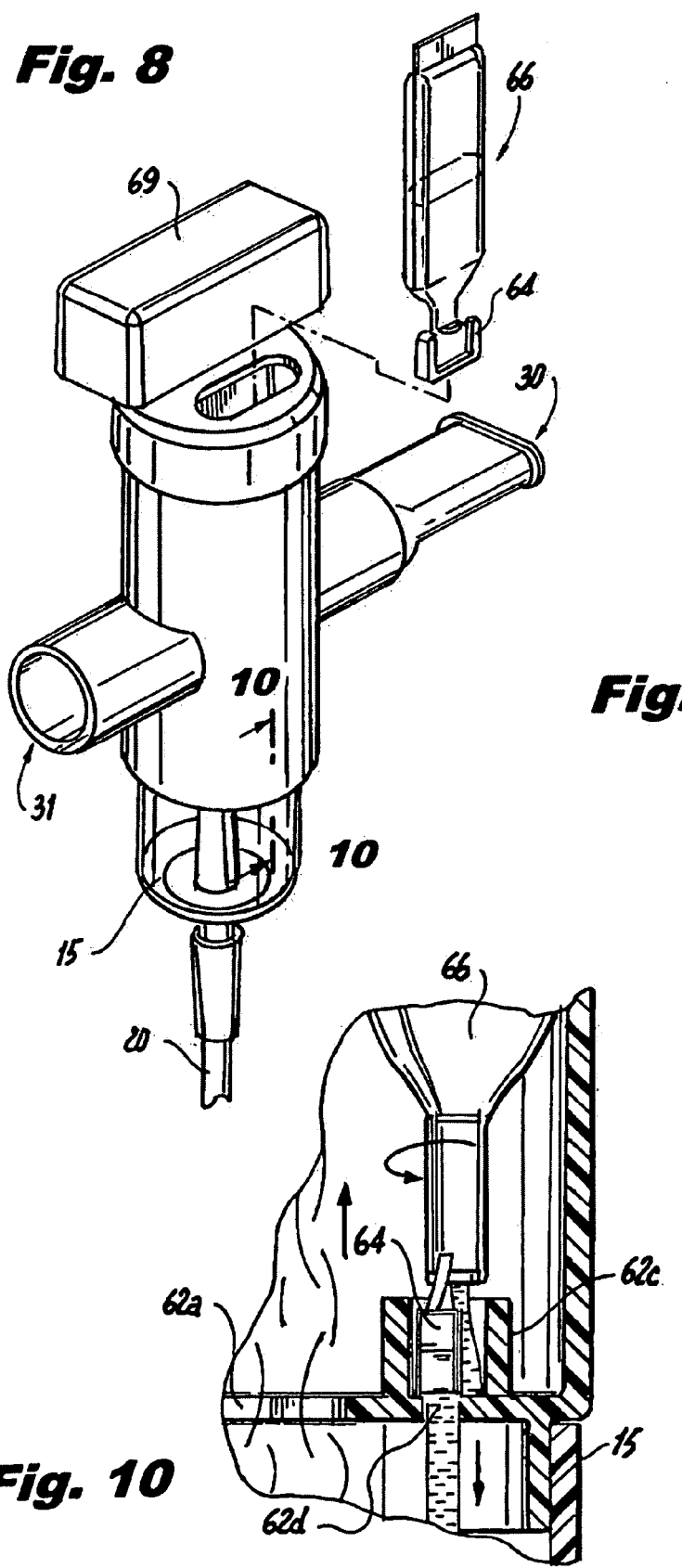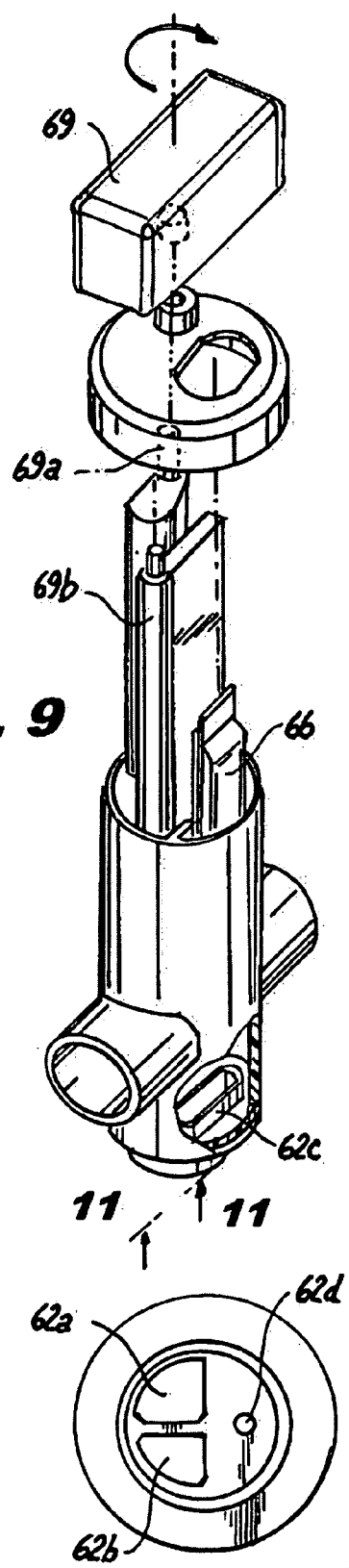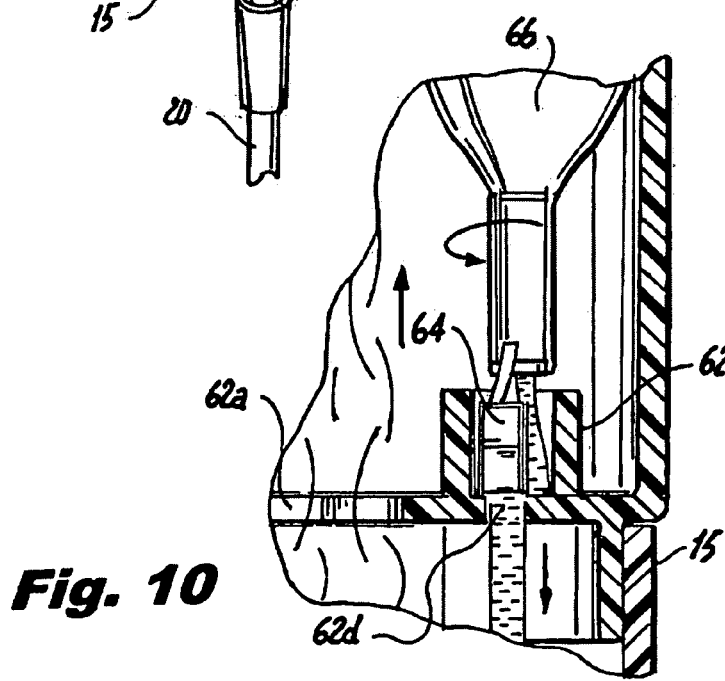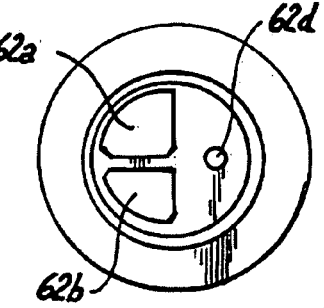
Fig. 8
Fig. 9
Fig. 10
Fig. 11

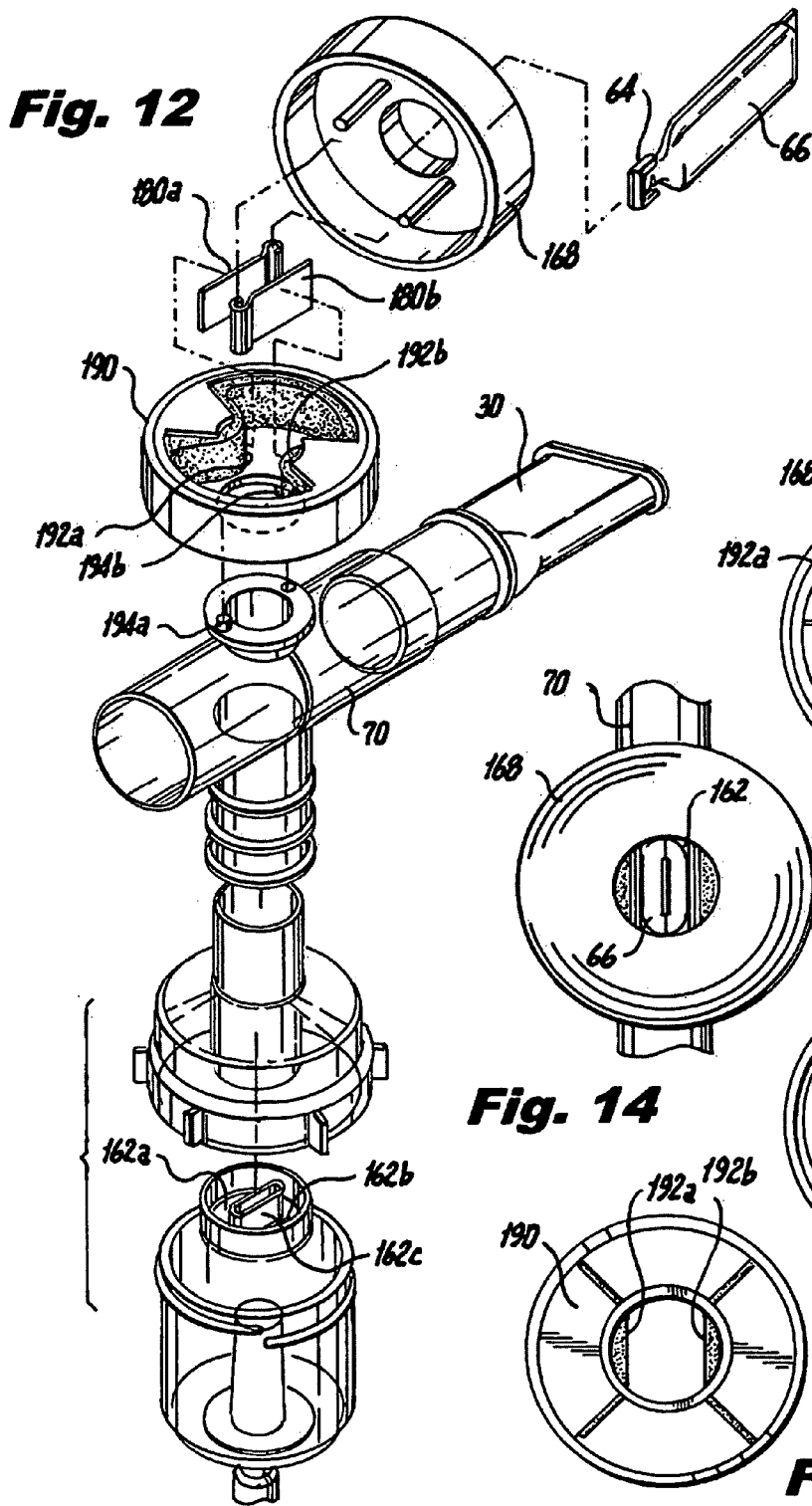

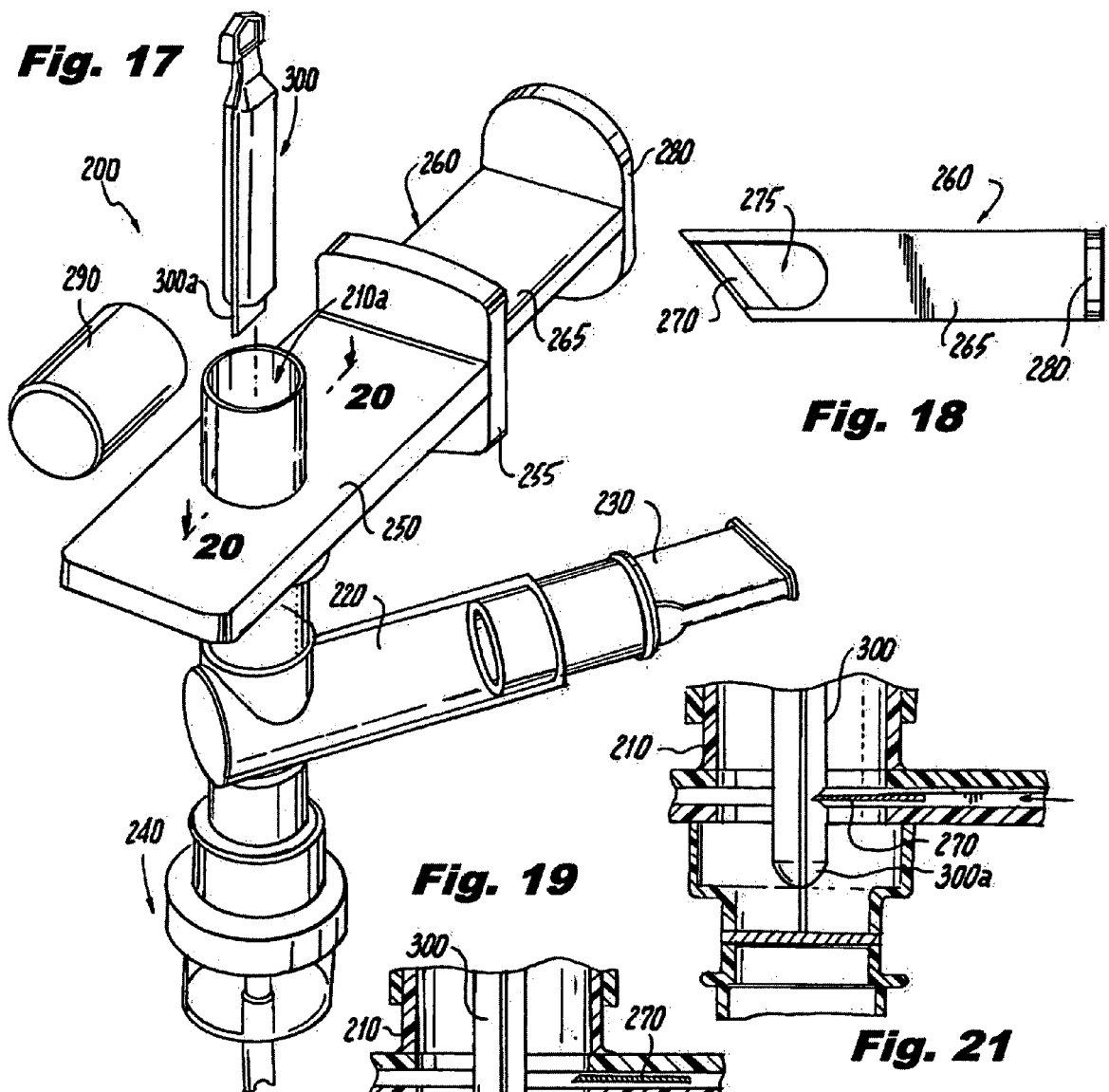
Fig. 17
Fig. 18
Fig. 19
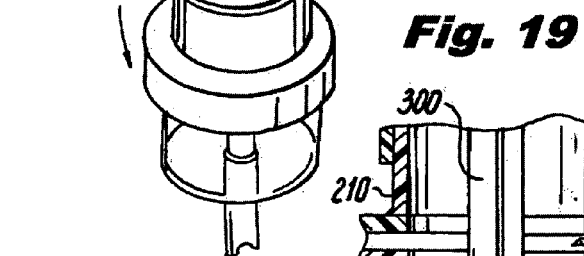
Fig. 21
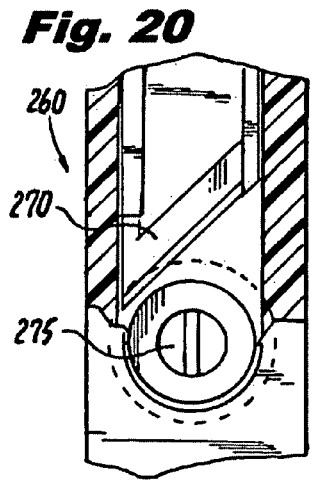
Fig. 20
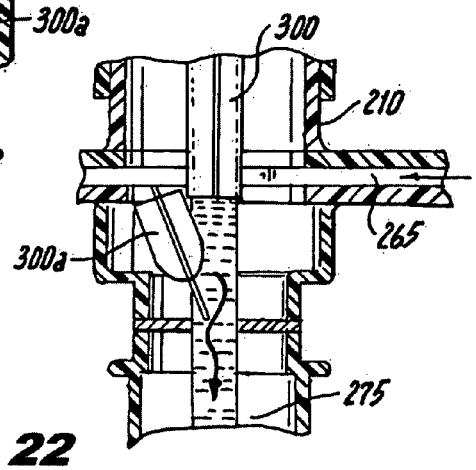
Fig. 22

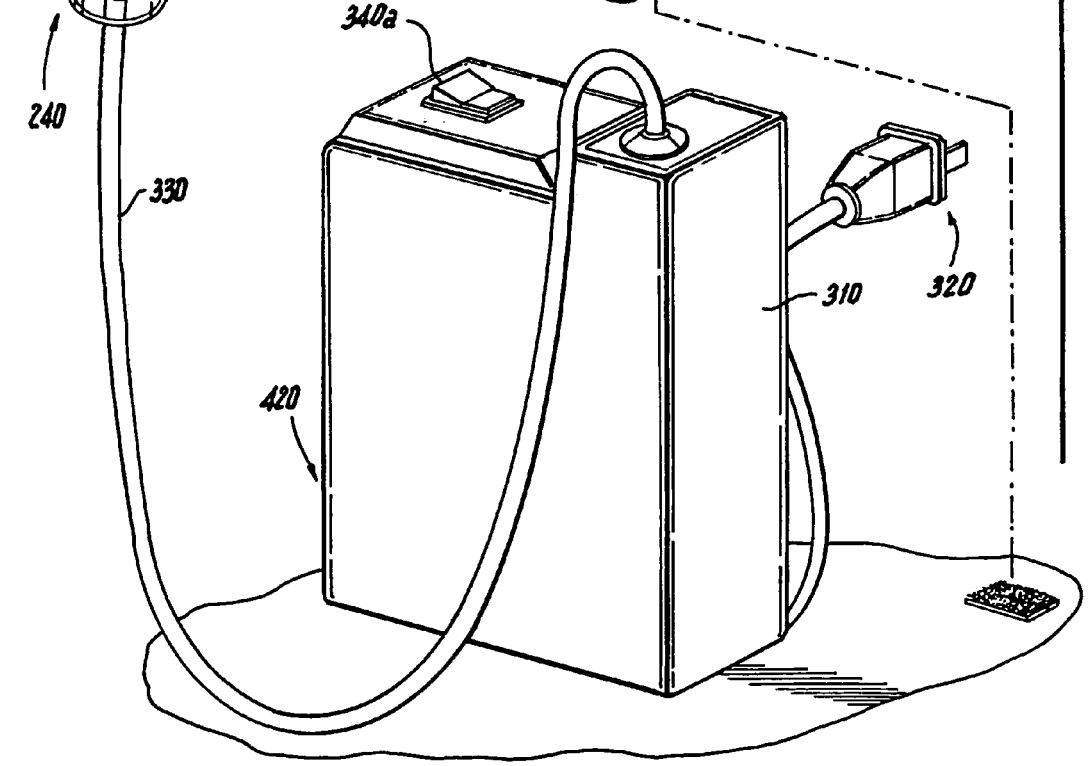

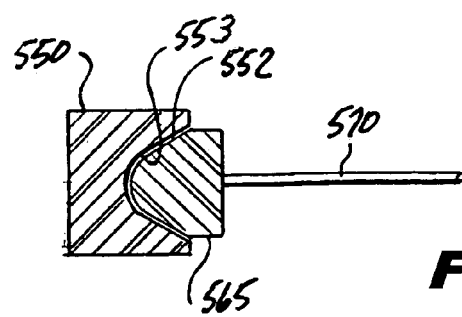
Fig. 24A
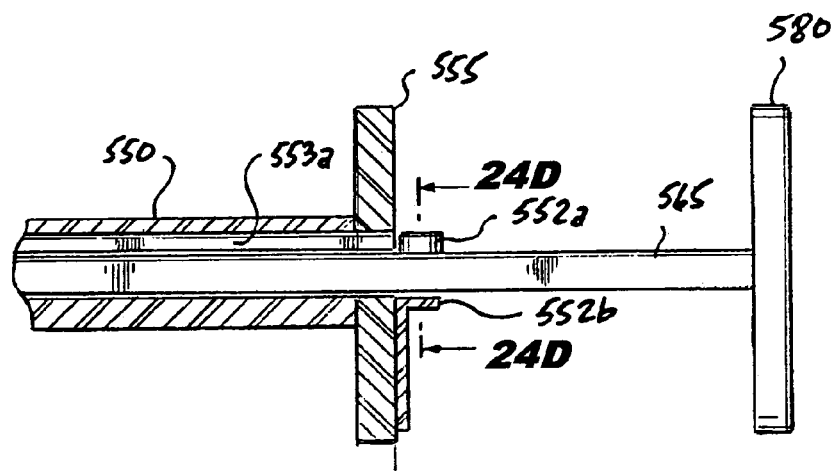
Fig. 24B
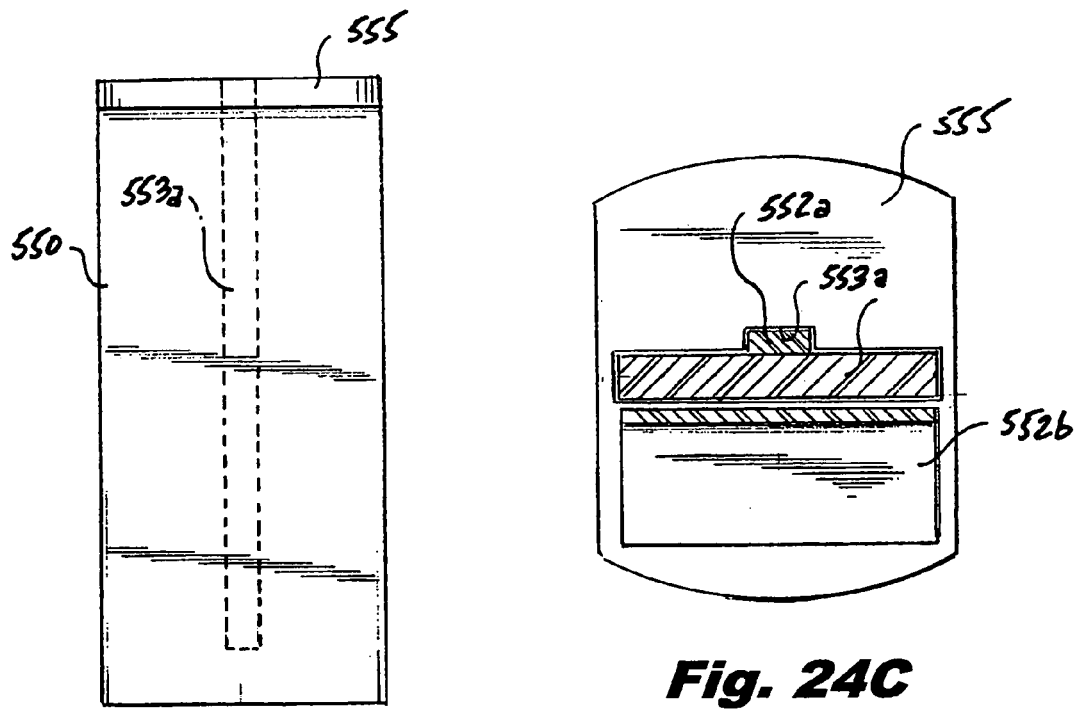
Fig. 24C
Fig. 24D

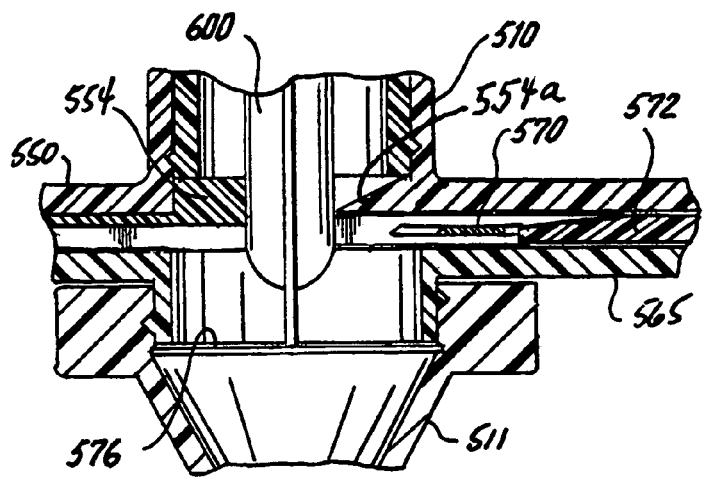
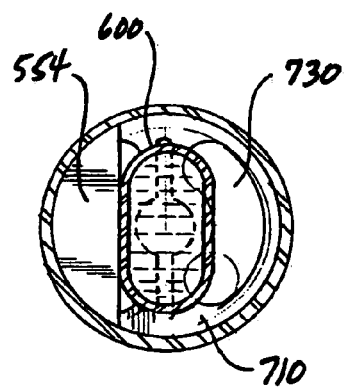
Fig. 26
Fig. 26A
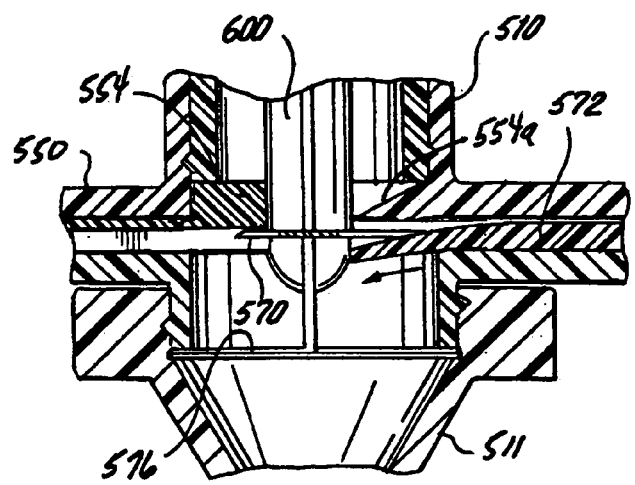
Fig. 27
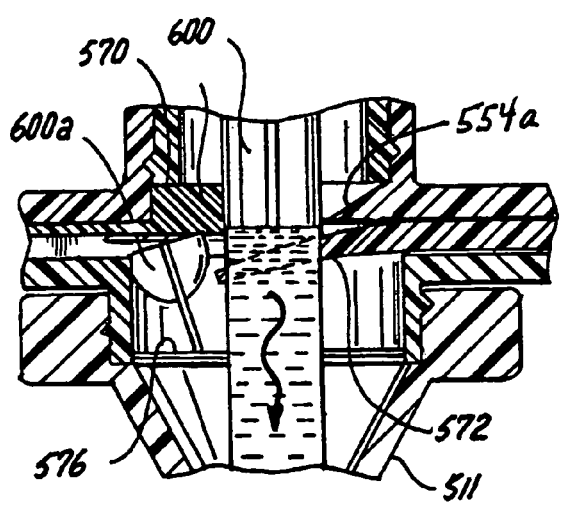
Fig. 28

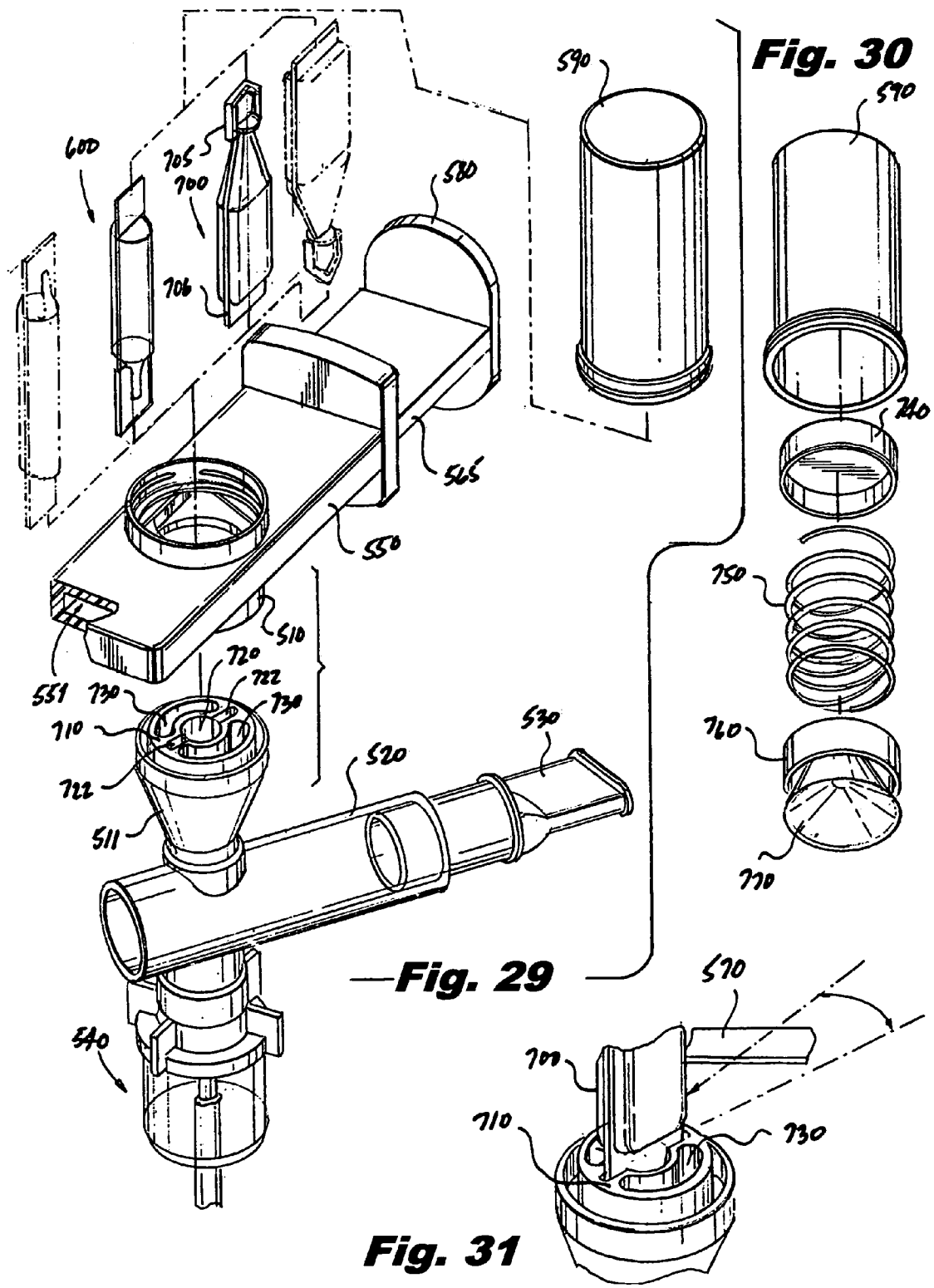

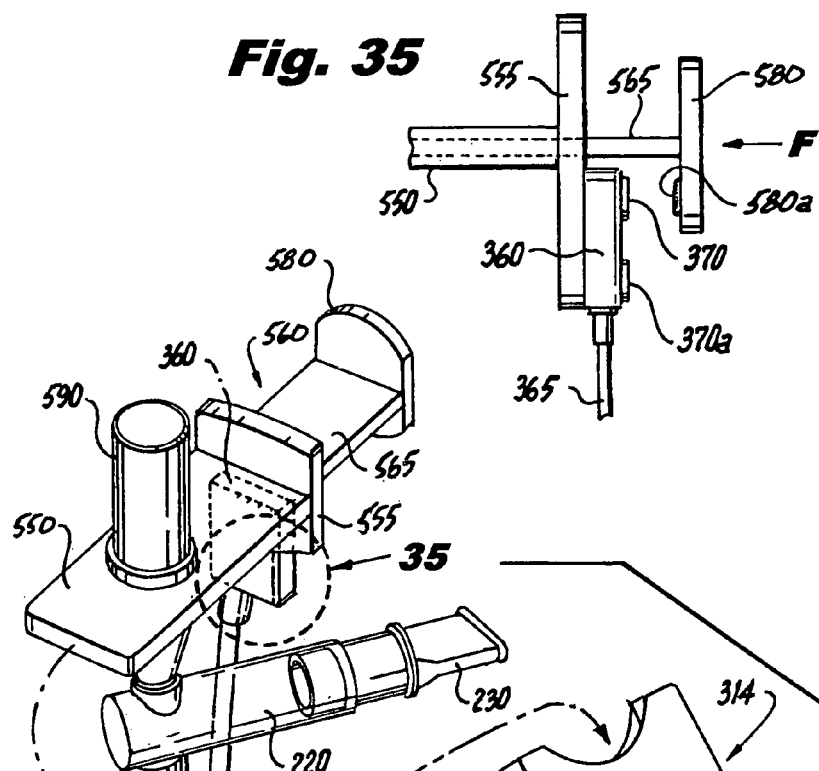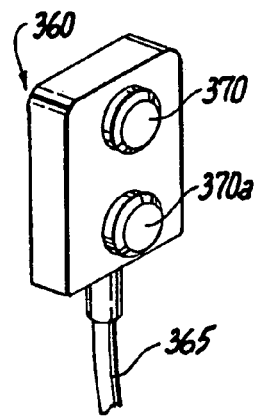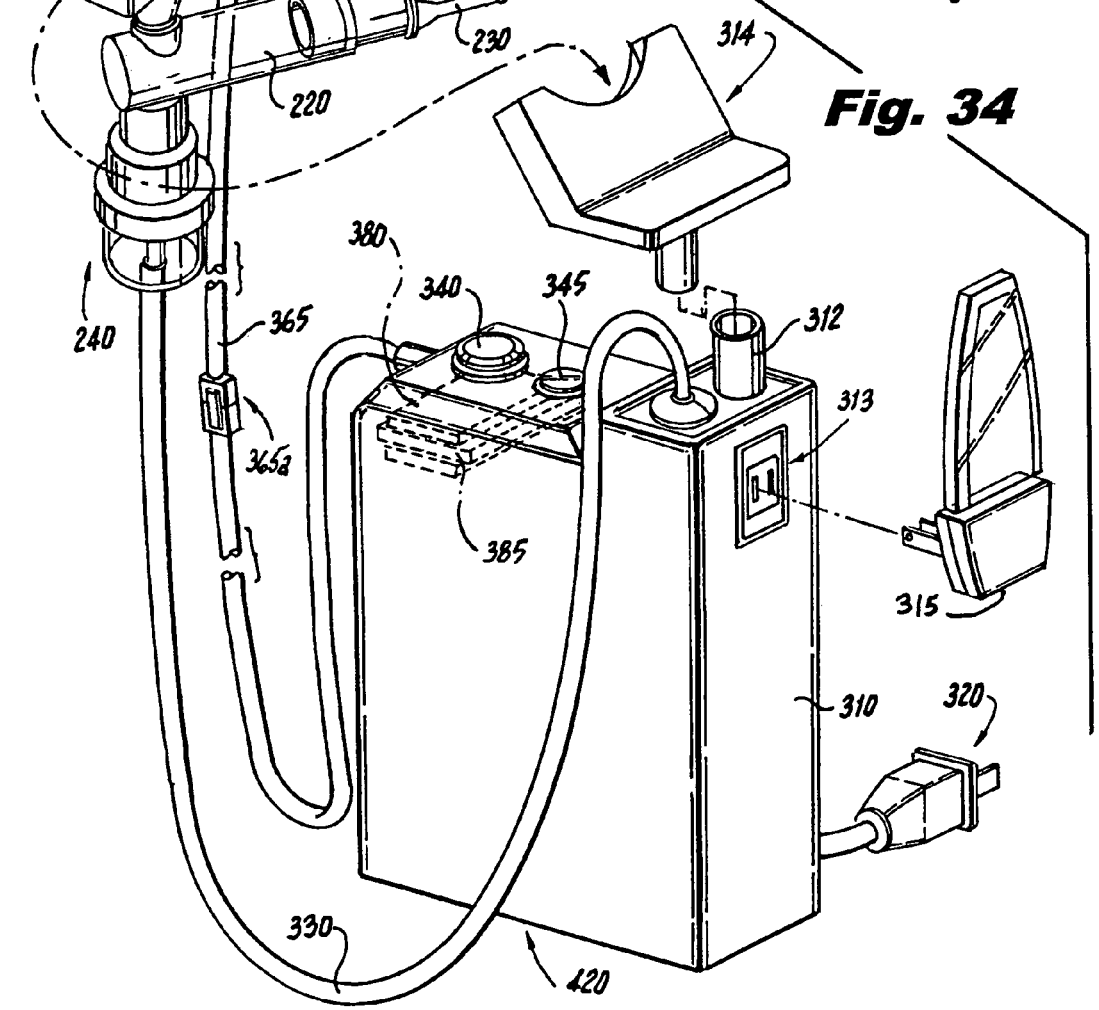

SEMI-AUTOMATIC EMERGENCY MEDICATION DOSE NEBULIZER

RELATED APPLICATIONS

This application is a continuation-in-part of application Ser. No. 11/901,628, filed Sep. 18, 2007, which application is incorporated by reference herein. This application claims priority in part under 35 U.S.C. §120 therefrom.

FIELD OF THE INVENTION

The present invention relates to a conventional nebulizer having a novel integral structure for conveniently delivering a dose of liquid medication to the conventional nebulizer's conventional nebulizing chamber

BACKGROUND OF THE INVENTION

Pulmonary medication may be needed by persons with breathing problems in a hurry. Typically a person experiencing an asthma attack is desperate to get medication. Often a single-shot hand-held rescue inhaler is medically inappropriate for treatment. In such cases, a misting nebulizer is needed. A misting nebulizer is an air pump device with a small plastic chamber attached to a mouthpiece. Prior art requires the nebulizer to be opened, liquid medication added to the chamber, the chamber closed and the pump started. The problem is that this series of steps requiring steady hands and manual dexterity may be difficult to achieve for an asthma attack sufferer who may be panicking because he/she can't breathe. Pulmonary medication may be needed by persons with breathing problems in a hurry. Typically a person experiencing an asthma attack is desperate to get medication. A nebulizer is an air pump device with a small plastic chamber attached to a mouthpiece. Prior art requires the nebulizer to be opened, liquid medication added to the chamber, the chamber closed and the pump started.

The problem is that this series of steps requiring steady hands and manual dexterity may be difficult to achieve for an asthma attack sufferer who may be panicking because he/she can't breathe. Pulmonary medication may be needed by persons with breathing problems in a hurry. Typically a person experiencing an asthma attack is desperate to get medication. A nebulizer is an air pump device with a small plastic chamber attached to a mouthpiece. Prior art requires the nebulizer to be opened, liquid medication added to the chamber, the chamber closed and the pump started.

OBJECTS OF THE INVENTION

It is an object of the present invention to provide a device for quickly and conveniently delivering a dose of liquid medication to the nebulizing chamber of a conventional nebulizer in an emergency.

It is a further object of the invention to provide reliable nebulized medication to a user in an emergency.

It is a further object of the invention to provide emergency nebulized medication to a user where the user is already in acute respiratory distress at the time the user locates the conventional nebulizer and has no person to assist with following the steps required to conventionally nebulize medication, to wit: (1) disassemble the nebulizer housing so as to expose the nebulizing chamber; (2) locate a container of liquid medication to be nebulized; (3) open the liquid medication container, being careful not to spill it; (4) squeeze capsule and pour the liquid medication directly into the nebulizing chamber without losing any of it through spilling outside of the nebulizer chamber; (5) reassemble the nebulizer housing; and (6) position the inhaler mouthpiece in the mouth so as to inhale the nebulized medication.

It is a further object of the present invention to simplify the conventional procedure required to be followed by the user of a medication nebulizer, which conventional procedure may be critically complex for a person suffering from acute respiratory distress at the time the user locates the conventional nebulizer.

It is a further object of the preferred embodiment of the present invention to provide a simplified reliable process for deploying a dose of liquid medication in a nebulizer, comprising the steps of (1) deploy the medication with a single twist of a screw cap; and (2) inhale the nebulized medication.

It is a further object of the present invention to provide a novel medication dose delivery device built-in and integrated with a conventional nebulizer to accomplish the result of simplified reliable delivery of the liquid medication to the conventional nebulizing chamber by convenient user deployment without the need to disassemble and reassemble the nebulizer and to open an pour liquid medication at the time of an acute respiratory emergency.

It is a further object of the present invention to provide a conventional nebulizer having a stored single does of liquid medication directly on board and integral with the conventional nebulizer in loaded-gun arrangement in preparation for use in an acute respiratory emergency.

It is a further object of the present invention to reduce the time needed for a person suffering an acute respiratory emergency to receive an effective dose of nebulized medication, particularly where the suffering person has no readily available assistance in using a nebulizer.

It is a further object of the present invention to provide a nebulizer device with a stored dose of liquid medication where deployment of that dose is accomplished by a simple manual operation by a user.

It is a further object of the present invention to provide a method for speeding relief to sufferers of acute respiratory distress by reducing the time and effort required to deploy liquid medication in a nebulizer.

It is a further object of the present invention to provide reliable faster and simpler relief to a sufferer of acute respiratory distress who is alone and without assistance by reducing the time and effort required to deploy liquid medication in a nebulizer.

In keeping with the present invention other objects will make themselves clear to users of the device and to those of skill in the art, and thus this invention is not limited to the objectives here enumerated, which are not exhaustively presented and are described merely by way of example.

SUMMARY OF THE INVENTION

In keeping with these objects and others which may become apparent, the present invention relates to a conventional nebulizer having a novel integral structure for conveniently delivering a dose of liquid medication to the conventional nebulizer's conventional nebulizing chamber, the novelty being in providing a new structural component integral with the structure of a conventional nebulizer, whereby the liquid dose capsule is opened upon manual activation of an activator, such as a plunger with a capsule opener.

It is further noted that, while the present invention is applicable to pulmonary conditions, such as asthma, it is contemplated that other medical conditions can be treated with misting medication where rapid deployment from a capsule is required. For example, nebulizers are described for use in treating diabetes with insulin in U.S. Pat. No. 5,451,569 of Wong et al, in treating human immuno-suppressed conditions in U.S. Pat. No. 7,388,076 and in cardiopulmonary resuscitation in U.S. Pat. No. 7,343,915 of Addington. Additionally U.S. Pat. No. 6,747,058 of Dedhiya et al describes dispensing medical marijuana through an aerosolizing nebulizer.

The preferable component is a chamber for vertically mounting the dosage capsule therein from above, wherein the capsule opener is a blade cutting the capsule or a twist opener with a torque application of twisting force to open the capsule to unload its contents directly into the misting chamber of the nebulizer. Besides the twisting force to open the capsule, the capsule is also subject to crushing force, to overcome the ambient air pressure nominally holding the medication fluid in the capsule, and preventing it from flowing freely through the narrow aperture at the discharge end of the medication capsule.

Alternatively, the plunger can automatically start the electrical components of the compression chamber for nebulizing a mist.

The novel structural component comprises a storage chamber for storing, in loaded-gun fashion, a dose of liquid medication on board the conventional nebulizer housing with a simple user-operable blade plunger capsule opener opening the medication capsule needed to deploy the medication into the conventional nebulizing chamber. The novel structure medication storage chamber generally has an open-aperture delivery end disposed in close proximity to the nebulizing chamber so that the liquid medication, when deployed by a user, flows reliably and directly into the nebulizing chamber.

The novel medication storage chamber of the non-preferred embodiment accepts a single disposable and user-replaceable cartridge containing a dose of medication to be nebulized in an emergency. The chamber is provided at its outer end with plunger having a capsule opener for a user to open the medication capsule. The capsule opener may be a blade to cut the capsule or a twister to twist open the capsule.

In the preferred embodiment, the severed capsule is held by a capsule holder with one or more fluid apertures.

In the blade cutting embodiment, optionally a rigid or slightly flexible capsule follower accompanies the cutting blade, to push the remnants of the severed capsule out of the way after severance of the capsule. Also the follower is used to separate the cut capsule to insure that all liquid is able to drain into nebulizer. The follower is small enough to insure fluid flow during the pushing of the severed capsule portions out of the way.

When the capsule is severed by the blade at an appropriate wide portion that ambient air pressure is not a factor, so the capsule does not need to be crushed. Fluid flows freely through the severed capsule without being crushed. The simplest emergency user-pressure means is a plunger one-hand aperture arrangement which permits a quick opening of the medication capsule to dispense the fluid therefrom.

The novel combination of medication dose capsule with a conventional nebulizer provided in the present invention addresses and solves the problem of what procedure must be followed by a patient having a breathing emergency, such as a severe attack of asthma, and needs a quick reliable dose of nebulized medication, particular where (1) no other person is available to assist the patient and (2) a single-shot hand-held nebulizer rescue inhaler is medically inappropriate for treatment.

BRIEF DESCRIPTION OF THE DRAWINGS

The present invention can best be understood in connection with the accompanying drawings. It is noted that the invention is not limited to the precise embodiments shown in drawings, in which:

FIG. 1 shows an exploded view of a prior art nebulizer disassembled to illustrate pouring of medication into the nebulizing chamber;

FIG. 2 shows a user operating a conventional prior art nebulizer by breathing through the mouthpiece;

FIG. 3 shows a perspective view of one embodiment having a conventional nebulizer having a novel built-in medication storage chamber extending outward from the housing of the nebulizer;

FIG. 4 shows a medication dose cartridge having an inner end with tapered shoulders so as to be capable of nesting within the medication storage chamber shown in FIG. 3; the medication cartridge has an outer end having means of accepting force for the purpose of ejecting the liquid medication contained in the cartridge through its inner end and into the nebulizing chamber;

FIG. 5 shows a detail of the embodiment of FIGS. 3 and 4, with the medication storage chamber extending outward from the nebulizing chamber through the wall of the nebulizer housing, having a medication dose cartridge therewithin and having a piston for application of force by a user to break the seal of the medication cartridge. The injection nozzle of the medication storage chamber is shown in close proximity to the nebulizing chamber within the housing;

FIG. 6 shows an exploded view of a second embodiment, having a vertical storage sleeve for a capsule of liquid medication, where the capsule is seated with its tear-off tab in close proximity to the conventional nebulizing chamber within the housing of the conventional nebulizer;

FIG. 7 shows a detailed crossectional view in cutaway of the twist open embodiment of FIG. 6;

FIG. 8 shows an exploded view of a third embodiment of the preferred embodiment, having a vertical storage sleeve for a capsule of liquid medication, where the capsule is seated with its tear-off tab in close proximity to the conventional nebulizing chamber within the housing of the conventional nebulizer;

FIG. 9 shows a top exploded view of the third embodiment of FIG. 8, having a vertical storage sleeve for a capsule of liquid medication, showing a lever twisting the capsule, while the tear-off portion of the capsule is seated and immobilized, so that twisting of the capsule causes a tear and crushing of the capsule between the tear-off portion and the fluid reservoir portion;

FIG. 10 is a close-up detail crossectional view in cutaway of the third embodiment in FIGS. 8 and 9, showing the rotation of the capsule while the tear-off portion is seated immobile in place;

FIG. 11 is a close-up detail bottom view of the sleeve of FIGS. 8, 9 and 10 showing the restraining stop means and mist-accommodating ports;

FIG. 12 is an exploded perspective view of an alternate fourth embodiment for a knob cam activation assembly for dispensing medication from a capsule;

FIG. 13 is a bottom view of the knob cam activation assembly shown in FIG. 12;

FIG. 14 is a top plan view of the knob activator thereof;

FIG. 15 is a bottom view of the knob activator as in FIG. 14;

FIG. 16 is a bottom view of the cam assembly shown in FIG. 12.

FIG. 17 is a perspective view of an alternate fifth embodiment for the nebulizer of this invention showing a flat blade plunger guide with a blade plunger in the extended position for slicing and cutting open the medication capsule;

FIG. 18 is a top view of the blade plunger assembly as in FIG. 17;

FIG. 19 is a crossectional side view detail thereof, showing the medication dosage capsule in the vertical storage chamber prior to the cutting operation;

FIG. 20 is a top plan crossectional detail view of the cutting blade approaching the medication dosage capsule to be severed;

FIG. 21 is a side crossectional view detail thereof, showing the cutting blade in contact with the medication dose capsule at the initiation of the cutting operation;

FIG. 22 is a side crossectional view detail of the medication dosage capsule in the vertical storage chamber just after having been cut with medication flowing through the plunger flow aperture into the lower section;

FIG. 23 is a perspective view of the entire nebulizer system of the fifth embodiment of this invention including the nebulizer assembly along with the compressor housing.

FIG. 24 is a perspective view of a sixth embodiment for a blade plunger assembly;

FIG. 24A is a close up side crossectional view showing a tongue and groove orientation sub-assembly, as viewed in dashed circle line "24A" of FIG. 24;

FIG. 24B is a close-up side crossectional detail view of another embodiment for an orientation sub-assembly for the blade plunger assembly;

FIG. 24C is a close-up front elevational view of the plunger portion thereof;

FIG. 24D is a top plan view of the plunger guide of the orientation sub-assembly of FIG. 24B;

FIG. 25 is a close-up perspective detail view of a follower paddle behind the cutting blade in the plunger assembly of FIG. 24;

FIGS. 26, 27 and 28 are a sequence of three side crossectional detail views showing the progress of the cutting blade from right to left in cutting through the medication dosage capsule and the release of the medication downward toward the nebulizer chamber;

FIG. 26A is a close-up top plan view of the capsule support region;

FIG. 29 is a perspective exploded view of a seventh embodiment of nebulizer with enhanced medication capsule holding features;

FIG. 30 is an exploded perspective view of coil spring hold-down elements within a storage chamber cap;

FIG. 31 is a perspective detail view of the medicine capsule base holder, showing a cutting blade approaching a medication capsule, wherein the angle and arrow lines depict a blade cutting angle orientation;

FIG. 32 is a side crossectional medicine capsule chamber prior to cutting;

FIG. 33 is a partial side crossectional of the medicine capsule chamber just after cutting showing medicine flow downward;

FIGS. 34-37 show a fully activated nebulizer system where activation of the capsule opening plunger also activates the nebulizer pump circuit;

FIG. 38 shows an auxiliary plug-in, not integrated starter box for automatically starting the misting compressor of the nebulizer inhaler of FIG. 17; and, FIG. 39 is a schematic diagram thereof.

LIST OF REFERENCE NUMERALS

10. Nebulizer Housing

11. Connecting Tube between nebulizer housing 10 and breather 25

14. Conventional medication dose container including:

15. Nebulizer chamber;

20. Compressed air supply line; and,

25. Conventional breather portion of conventional nebulizer;

30. Conventional mouthpiece at proximal end of conventional breather 25

31. Open distal end of conventional breather 25.

32. Inside Surface of Novel Storage Chamber.

35. Novel storage chamber for medication dose.

36. Inner end of medication storage chamber 35.

37. Outer end of medication storage chamber 35.

38. Tapered open-ended nozzle at inner end 36 of medication storage chamber 35.

40. User-Removable user-replaceable medication dose cartridge containing a dose of liquid medication to be nebulized.

41. Outer end of Medication dose cartridge 40.

42. Inner end of Medication dose cartridge 40.

43. Pressure seal at inner end 42 of Medication dose cartridge 40.

44. Elastomerically Sealed Piston at outer end 41 of cartridge 40.

45. Open reduced-diameter inner end of Medication dose cartridge 40.

47. Tapered inner shoulders of medication Cartridge 40.

50. Grooved piston rod.

52. Finger engagement wings.

55. Stop for engaging groove of Piston Rod 50

56. Pressure plate at the end of Piston Rod 50 for application of user force.

62. Vertical medication storage sleeve 62.

62*a*, 62*b*. Slots in sleeve 62 to allow fluid to enter reservoir 15

62*c*. Restraining stop means for tear off portion of capsule 66

62*d*. aperture for fluid flow into reservoir 15

64. Tear off tab.

66. Medication dose capsule.

68. Screw cap activating handle.

69. Activating lever handle.

69*a*. Activating lever handle rod.

69*b*. Activating lever handle paddle.

70. Inhaling pipe.

162*a*. Mist port.

162*b*. Mist port.

162*c*. Restraining stop means.

168. Knob activator.

180*a*. Capsule pincher blade.

180*b*. Capsule pincher blade.

190. Cam assembly.

192*a*. Cam contact element.

192*b*. Cam contact element.

194*a*. Rotation stop element.

194*b*. Reciprocating rotation stop element.

200 Nebulizer assembly with blade cutter.

210 Vertical storage chamber.

Figure 1:
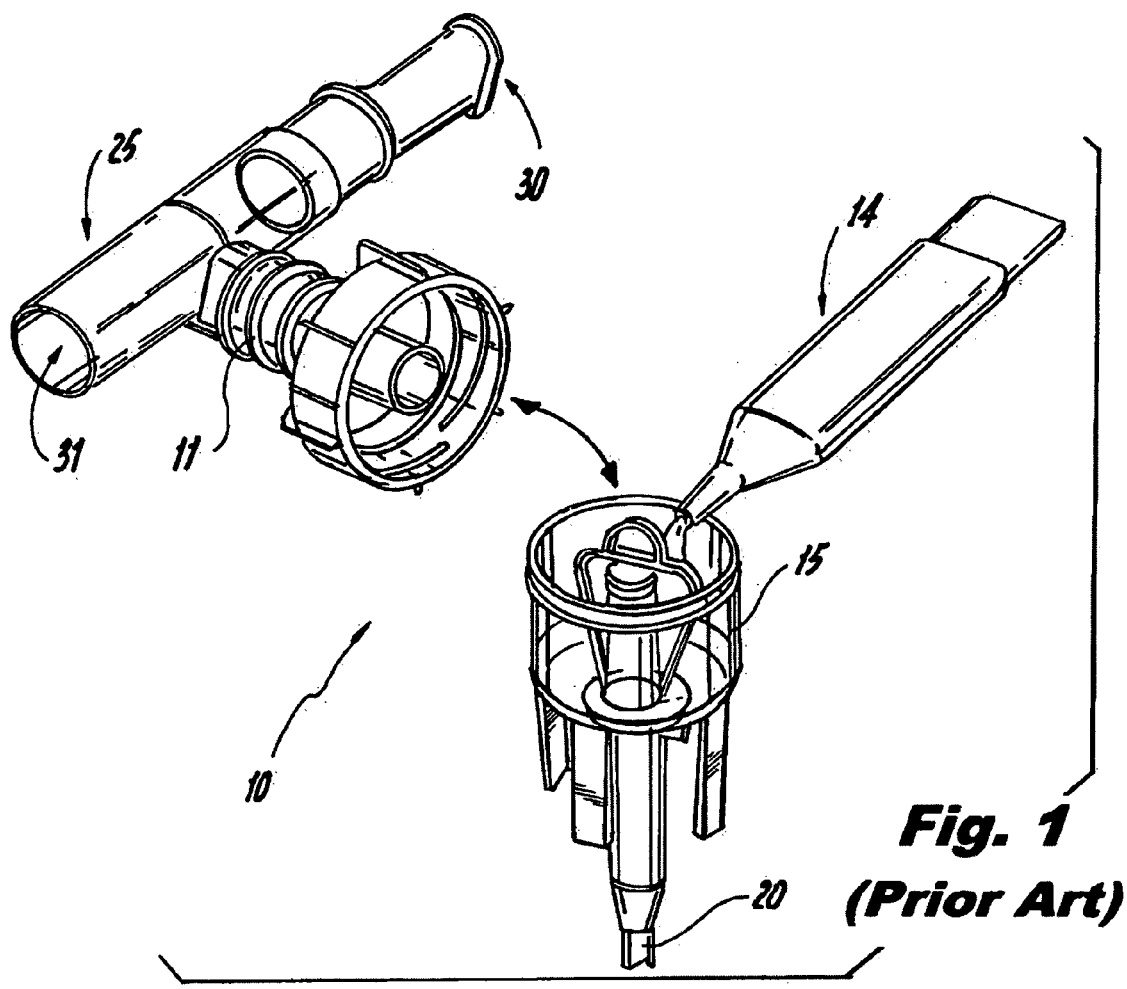

220 Inhalation tube.
230 Mouthpiece.
240 Conventional nebulizing chamber.
250 Flat blade plunger guide.
255 Fixed finger grip.
260 Blade plunger assembly.
265 Flat blade plunger.
270 Cutting blade.
275 Plunger flow aperture.
280 Plunger finger grip.
290 Perforated storage chamber cap.
300 Medication dosage capsule.
300a Severed distal end portion of medication capsule 300.
310 Conventional compressor housing.
311 Integrated compressor housing.
312 Locator light indicator and holder support.
313 Night light plug receptacle.
314 Nebulizer holder.
315 Night light.
320 Electrical wall plug.
330 Compressed air line.
340 Manual compressor switch.
340a Manual rocker switch of conventional compressor
345 Indicator lamp.
360 Plunger switch.
365 Plunger switch cable.
365a Switch cable connector.
370 "ON" button of plunger switch
370a "OFF" button of plunger switch
380 Relay.
385 Transformer.
390 Relay coil.
395 Relay contacts.
410 Compressor motor.
420 Air compressor.
500 Nebulizer assembly with blade cutter and pusher.
510 Vertical storage chamber.
510a Capsule retaining guide opening
510b Capsule retaining guide
520 Inhalation tube.
530 Mouthpiece.
540 Conventional nebulizing chamber.
550 Flat blade plunger guide.
551 Hollow pocket in plunger guide 550.
552 Inner wall tongue.
552a Inner wall protrusion button.
552b External misorientation stop.
553 Inner wall groove.
553a Inner wall top groove.
554 Capsule stabilizer block.
554a Sloping capsule guide.
555 Fixed finger grip.
556 Capsule guide
560 Blade plunger assembly.
565 Flat blade plunger.
570 Cutting blade.
572 Follower paddle of cutting blade 570.
573 Aperture in blade plunger 570.
575 Hollow discharge tube.
576 Screen.
580 Plunger finger grip.
590 Storage chamber cap.
600 Medication dosage capsule.
600a Severed distal end portion of medication capsule 600.
700 Alternate style medication dosage capsule.
705 Pointed top end of dosage capsule 700.
710 Medication capsule base holder.
720 Central hole with slots in base holder.
722 Slots of control hole 720.
730 Peripheral holes in base holder to permit medication flow.
740 Top fixed spring retainer.
750 Coil spring.
760 Bottom movable spring retainer.
770 Conical top holder for medication capsule.
800 Auxiliary power box.
802 Nebulizer plug outlet.
803 Night light outlet.

DETAILED DESCRIPTION OF THE INVENTION

In keeping with the objects of the invention, the present invention provides a conventional nebulizer having a built-in (and thus integral) novel storage structure for storing a dose of liquid medication in preparation for an emergency. The liquid medication is conveniently delivered to the conventional nebulizer's conventional nebulizing chamber.

A conventional nebulizer is used to aerosolize liquid medication and deliver the aerosol for inhalation by a user. Although both are typically used for treating pulmonary medical conditions such as asthma, a conventional nebulizer differs from hand-held inhaler sprayers in that the hand-held aerosolizer generally contains multiple doses of medication, has a propellant permanently loaded within it, and is indicated for use where a single aerosolized dispensed quantity comprises the intended dose of medication for use by a patient.

It is critical to accurately time the dispensing shot from a hand-held medication inhaler to coincide with a user's inspiration, so as to ensure that the medication actually reaches the lungs of a user. Mistiming of the dispensing shot from a handheld inhaler can result in a short dose of medication or in no dose at all.

A conventional nebulizer, in contrast, has no stored medication at all. It is comprised of a nebulizing chamber, an air pump and an inhaler. The air pump, usually electrically driven, supplies a stream of compressed air through a conduit to a nebulizer housing. The housing is generally cylindrical, has a top and bottom part that can be separated by a user, and the top part has an upwardly projecting extension that ends in an inhaler. The inhaler is generally a horizontally disposed tube with an open distal end and a proximal end that is an open-ended mouthpiece.

The conventional nebulizer housing contains a nebulizing chamber. The chamber is basically a vertical cylinder with an open top for receiving a dose of liquid medication. The chamber has an air-stream inlet in the bottom. Compressed air from the air pump is conveyed to the chamber's bottom air inlet through a conduit. The compressed air enters the bottom of the nebulizing chamber and is then mixed with the dose of liquid medication, causing the medication to become nebulized into an aerosol. There is an open airflow between the nebulizer chamber and an upwardly extending short tube leading to a T-connection with a horizontal tube open at both ends that comprises an inhaler pipe with a breather mouthpiece at one end. One open end of the inhaler pipe comprises a distal end, opposite to a proximal end which comprises the mouthpiece shaped to fit into the mouth of a user.

The inhaler pipe is in open airflow with the nebulizer chamber. When a user inhales through the proximal open end of the mouthpiece, air is urged into the open distal end and into the proximal end of the mouthpiece. The user's inhalation effort also urges air from the nebulizer chamber, containing nebulized medication to rise up the connecting tube and to enter the proximal end of the mouthpiece.

The user thus inhales nebulized liquid medication, and the user may do so with inhalations repeated as needed over a period of time sufficient to get relief from respiratory symptoms that put the user into acute-distress, such as an asthma attack.

Thus an important difference between a conventional nebulizer and a hand-held inhaler is that the hand-held device is intended to deliver a single dose of medication intended to treat the entire episode of acute respiratory distress. The user must time the dispensing shot of the hand-held nebulizer to coincide with a breath inspiration or the effect of the device is defeated and the medication shot is wasted. In contrast, a conventional nebulizer provides the ability for an acute respiratory sufferer to breathe as many times as needed to receive sufficient nebulized medication into the lungs to alleviate the acute distress symptoms. The conventional nebulizer thus does a different job as compared to the hand held inhaler.

In additional comparison, handheld inhalers typically contain numerous doses of medication while a conventional nebulizer contains no medication at all.

A critical problem solved by the present invention is that, while medication delivered by a conventional nebulizer could be more effective than medication delivered by a hand-held inhaler due to the availability of repeated inhalations of medication with the conventional nebulizer, there remains an important shortcoming, which is addressed by the inventive step of the current invention.

In order to use a conventional nebulizer it is necessary for a user, or someone assisting the user to (1) disassemble the nebulizer housing by removing its top so as to expose the nebulizing chamber; (2) locate a separately stored container of liquid medication to be nebulized; (3) carefully open the liquid medication container so as not to spill it; (4) pour the liquid medication directly into the nebulizing chamber without losing any of it through spilling into the nebulizer housing; (5) reassemble the nebulizer housing; and (6) position the inhaler mouthpiece in the mouth so as to inhale the nebulized medication.

A problem arises in that use of a nebulizer is not going to be sought until a person is already in acute respiratory distress. Otherwise, problems of nebulizer overuse, overmedication, medication side effects and a search for alternate pulmonary therapy modalities will all become concerns for a patient. Therefore, use of a conventional nebulizer implies that a user is experiencing acute pulmonary symptoms, is in acute distress, and is experiencing an emergency.

Persons suffering acute respiratory distress are routinely subject to being fearful, frightened, or fully panicked. Fear, fright and panic are well known to degrade performance on tasks requiring some level of skill in eye-hand coordination tasks. When seeking the use of a conventional nebulizer, then, a user is required to locate a separate container holding a dose of liquid medication, open the nebulizer, open the medication container, pour the liquid into the nebulizer chamber, and re-assemble the nebulizer housing. The aforedescribed sequence of steps can be difficult or impossible for a fearful, frightened or panicked sufferer of acute respiratory distress. An important consideration is that there will almost certainly be occasions when a person experiencing acute need of a conventional nebulizer is alone and without anyone to assist. It is just these occasions where a conventional nebulizer may be available but be impossible for a user to operate.

To solve the problem of user inability to operate a conventional nebulizer in an emergency, the present invention presents a simple solution: construct a conventional nebulizer than has a built-in stored dose of liquid medication and make that liquid dose injectable into the nebulizer chamber with either a simple twist of a screw cap (preferred embodiment of the present invention) or a single stroke of user force (non-preferred embodiment). As provided in the present invention the user will not be required to disassemble or reassemble the housing of a conventional nebulizer; will not be required to locate a separately stored container of liquid medication; will not be required to open the separate medication container; and will not be required to pour the liquid medication into the nebulizer chamber.

According to the present invention, a conventional nebulizer will have added to its housing a storage chamber, preferably cylindrical, for storing, in loaded-gun fashion, a dose of liquid medication on board the conventional nebulizer housing.

In the preferred embodiment of the present invention the novel storage chamber for the medication capsule is a substantially cylindrical sleeve with an open top aperture projecting vertically downward from the inhaler pipe to a point slightly above the conventional nebulizer chamber within the housing of a conventional nebulizer. The sleeve's diameter is small enough so as not to interfere with the conventional nebulizer's free flow of air from the nebulizer chamber, up the conventional neck of a nebulizer and into the conventional inhaler pipe of a nebulizer. The medication capsule storage sleeve merely occupies a portion of the air passage between the nebulizer chamber and the inhaler pipe and thus in no way does the storage sleeve seal or impede the conventional free flow of air within what is otherwise a conventional nebulizer.

In one embodiment of the present invention the novel medication storage chamber (as with the preferred embodiment, the storage chamber of the non-preferred embodiment is also sleeve-like); however, instead of extending vertically as does the sleeve of the preferred embodiment, the storage chamber of the non-preferred embodiment generally projects outwardly from an inner delivery end in proximity to the nebulizing chamber, through the wall of a conventional nebulizer housing, and extends to an outer user-access end.

In the non-preferred embodiment the novel structure medication storage chamber generally has a tapered-nozzle open-aperture delivery end disposed in close proximity to the nebulizing chamber so that the liquid medication, when deployed by a user, is injected reliably and directly into the nebulizing chamber.

In the present invention the novel medication storage chamber accepts a single disposable and user-replaceable capsule containing a dose of liquid medication to be nebulized in an emergency. The chamber is provided at its outer end with pressure means for a user to exert a stroke of physical force upon the outer end of the medication chamber so as to exert force or slicing against the medication cartridge. The capsule is generally cylindrical with an end sized to match and fit within the medication storage chamber. In the non-preferred embodiment an outer end of the medication capsule is capable of accepting force from a manually-operated piston.

The medication dose capsule has a seal that is capable of rupture upon application of pressure, the seal being located at an inner end of the capsule, disposed at or near the inner end of the medication storage chamber. The preferable emergency user-pressure means is a piston arrangement, where the piston is integral with the medication capsule, is elastomerically sealed, and accepts a push-force from a piston rod. The easily recognized example of this is a medical syringe.

In another embodiment, insertion of the medication capsule within a rotatable knob cam activation assembly facilities bursting of the seal of the medication reservoir capsule. In a preferred embodiment, the medication capsule is opened by a sliding blade activated by a plunger.

The novel combination of the present invention addresses and solves the problem of what procedure must be followed by a patient having a breathing emergency, such as a severe attack of asthma, and needs a quick reliable dose of nebulized medication, particular where (1) no other person is available to assist the patient and (2) a single-shot hand-held nebulizer is medically inappropriate for treatment.

DETAILED DESCRIPTION OF THE DRAWINGS

FIG. 1 is an exploded view of a prior art conventional nebulizer housing 10 shown disassembled. Conventional medication container 14 is shown adding liquid medication to conventional nebulizing chamber 15. In the event of a respiratory emergency, a user would have to locate a separate container of liquid medication 14, then open it, then disassemble (as shown) the portions of the nebulizer housing 10, then pour the liquid medication from its separate container 14 into nebulizer chamber 15, then reassemble nebulizer housing 10 before being able to inhale nebulized medication through proximal end of conventional mouthpiece 30 which is part of conventional breather 25, breather 25 having an open distal end 31 opposite to proximal end 30.

When a user has pour medication into nebulizer chamber 15 and reassembled housing 10, then conventional air supply line 20 supplies a stream of compressed air to nebulizer chamber 15 causing the liquid medication to become nebulized and urging the nebulized medication upward through connecting tube 11 so as to be available for user inhalation through proximal end mouthpiece 30.

Figure 2:
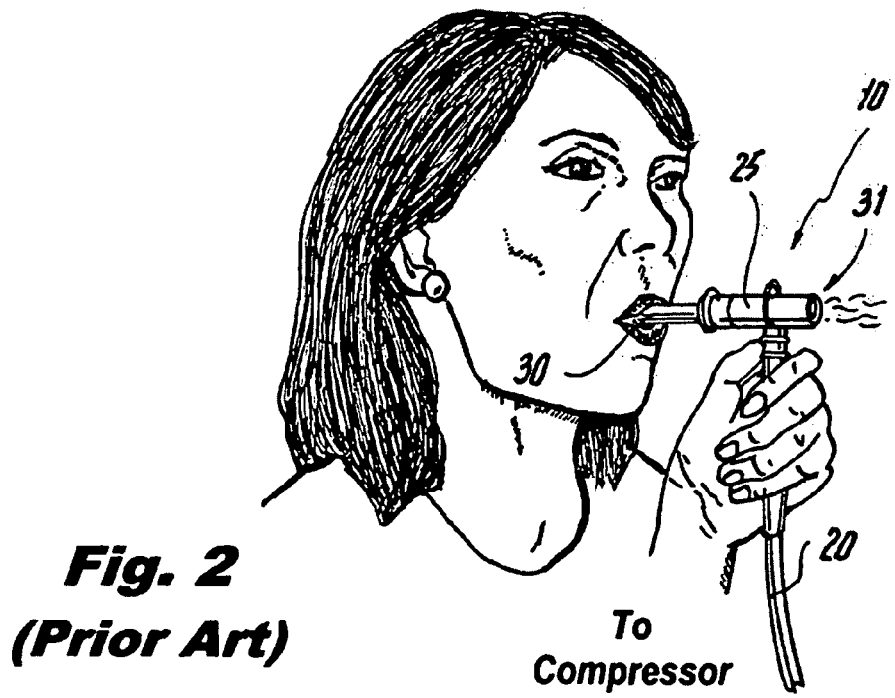

FIG. 2 shows a perspective view of the prior art conventional nebulizer in use. A user inserts the proximal mouthpiece end 30 of breather 25 into the mouth and inhales. Nebulizer housing 10 [concealed by the user's hand in the drawing] furnishes nebulized (aerosolized) medication to the user for as many repeated inhalations as the user may need for alleviation of an acute respiratory emergency. Air supply lines 20 is shown extending upwardly but the user's hand conceals the intersection of air supply line 20 with the bottom of the nebulizer chamber 10.

In one embodiment of the present invention, the novel medication storage chamber generally projects outwardly from an inner delivery end in proximity to the nebulizing chamber, through the wall of a conventional nebulizer housing, and extends to an outer user-access end.

Figure 3:
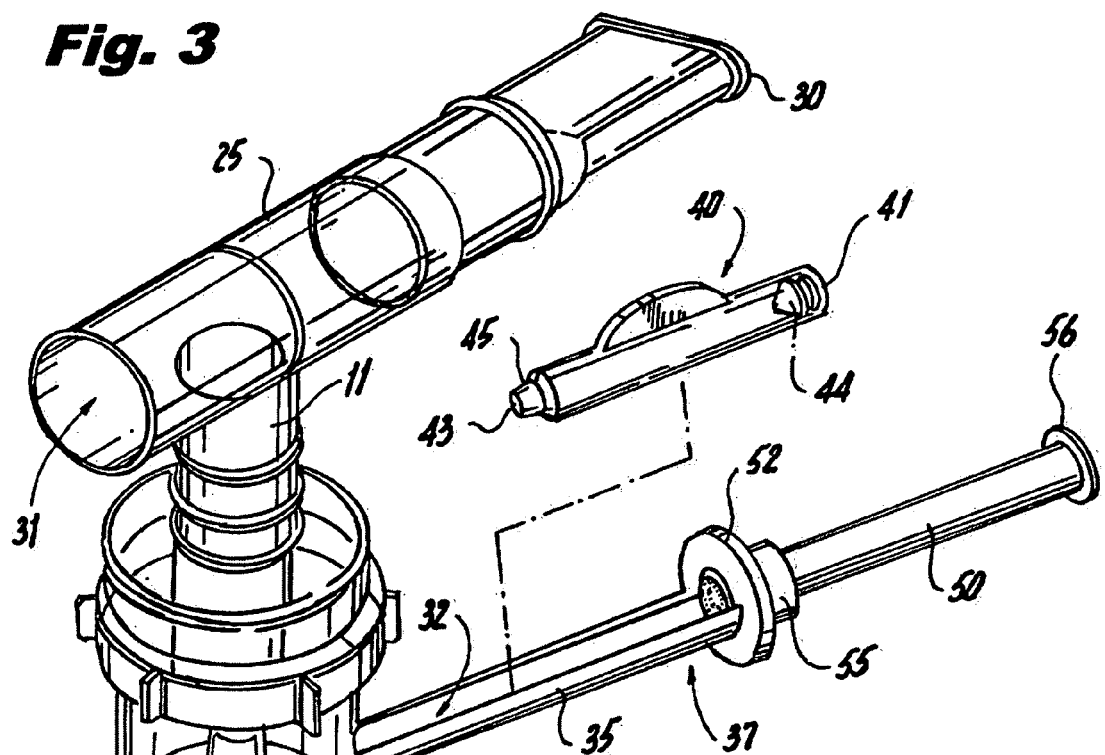

FIG. 3 shows a first embodiment of the present invention with a conventional nebulizer housing 10 fitted with novel integral (i.e., built-in) medication storage chamber 35. Storage chamber 35 is capable of receiving removable medication dose cartridge 40. Both chamber 35 and matching cartridge 40 are elongated, preferably cylindrical and both have matching inner and opposite outer ends. The inner end 36 of storage chamber 35 is disposed within nebulizer housing 10 while outer end 37 of chamber 35 is outside of nebulizer housing 10. Chamber 35 is fixed in a position that places its inner end 36 in close proximity to nebulizing chamber 15. The preferably cylindrical body of chamber 35 points radially outward from nebulizing chamber 15 so that outer end 37 of medication storage chamber 35 is outside of and spaced apart from nebulizer housing 10.

Medication storage chamber 35 is provided with open-ended tapered nozzle 38 at its inner end 36, nozzle 38 being in close proximity to nebulizing chamber 15 so as to reliably inject a dose of liquid medication from cartridge 40 upon user application of a single inwardly directed pressure stroke to pressure plate 56 of grooved piston rod 50, disposed within medication storage chamber 35, at the outer end 37 of said storage chamber.

Medication cartridge 40 is provided with tapered inner end 42 tapered to open end 45. Pressure seal 43 is located at inner end 42 of cartridge 40 while elastomerically sealed piston 44 is located at the outer end of cartridge 44. Upon user application of a single stroke of inward pressure on pressure plate 56 at the outer end of piston rod 50 (user grasps Finger Engagements Wings 52 for convenience), contact is made between grooved piston rod 50 and piston 44 resulting in an increase in hydraulic pressure on seal 43. Tapered shoulders 47 of cartridge 40 contact and engage tapered nozzle 38 of medication storage chamber 35, causing cartridge 40 to become seated firmly within cartridge 35 when a user applies manual pressure to pressure plate 56 of grooved piston rod 50.

Seal 43 is manufactured so as to burst upon user force application on pressure plate 56 of grooved piston rod 50. When seal 43 bursts, pressure from grooved piston rod 50 causes injection of liquid medication from cartridge 40 into nebulizing chamber 15. The remainder of the nebulizing operation is conventional.

Figure 4:
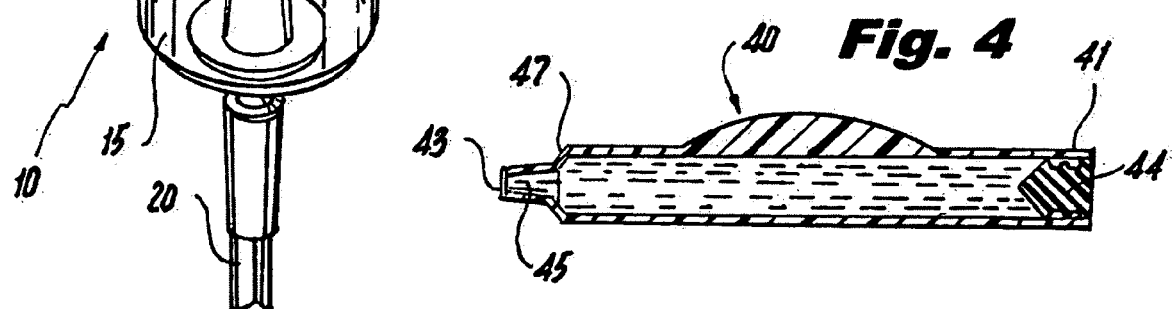

FIG. 4 shows the first embodiment of the present invention with a detail of removable medication dose cartridge 40, having pressure seal 43 disposed at inner end 42, open end 45 is comprised of the tapered shoulders 47 at inner end 42 of cartridge 40 and outer end 41 contains movable elastomerically sealed piston 44. Piston 44 receives pressure from grooved piston rod 50. In response, piston 44 moves in an inward direction applying hydraulic pressure to the liquid medication contained within the body of cartridge 40. In turn the hydraulic pressure causes seal 43 at the inner end of cartridge 40 to burst. When seal 43 ruptures, liquid medication is forced under piston pressure to be injected into nebulizing chamber 15.

Figure 5:
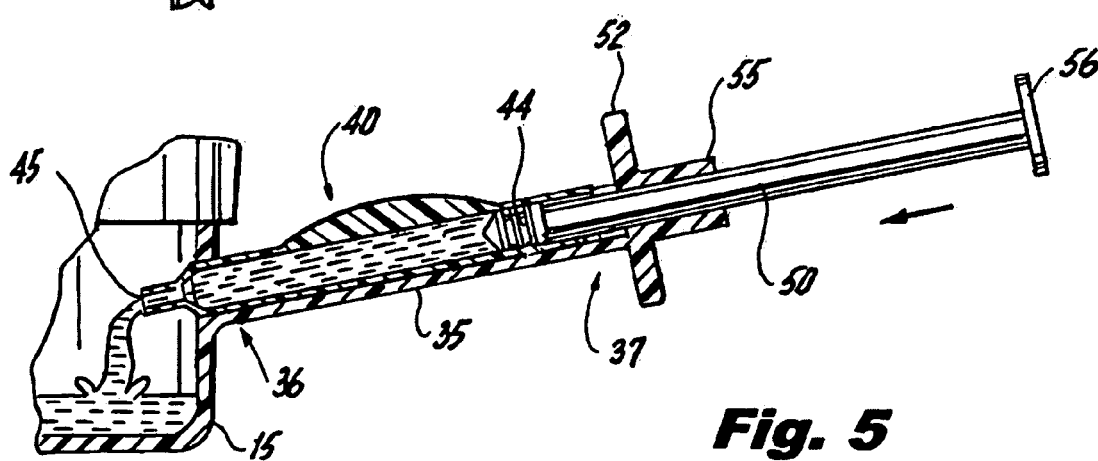

FIG. 5 shows the first embodiment of the present invention with a cut away side view detail of medication storage chamber 35 intersecting nebulizer housing 10 so as to have inner end 36 of chamber 35 in close proximity to nebulizing chamber 15 for reliable injection into chamber 15 of liquid medication from open inner end 43 of cartridge 40 upon application of a single stroke of inward user pressure upon pressure plate 56 of grooved piston rod 50, the force being transmitted to piston 44 of cartridge 40. Stop 55 engages groove on piston rod 50, preventing piston rod 50 from coming out of medication storage chamber 35.

As shown in a second alternate embodiment shown in FIGS. 6 and 7, the novel medication storage sleeve 62 projects vertically downward from the top of horizontal inhaling pipe 70 extending downwardly into the nebulizer housing 10 to a point just above the nebulizing chamber 15. A medication dose capsule 66 is an elongated substantially cylindrical container oriented vertically within sleeve 62.

Capsule 66 is user inserted and user removed respectively to and from sleeve 62. Capsule 66 is intended to be stored in sleeve 66 until used, and then removed and replaced in preparation for a next use of the nebulizer.

Capsule 66 has a lower end tear off tab 64. Sleeve 62 has lower end stop means 62c to engage tear off tab 64 to prevent tab 64 from turning when torque is applied to capsule 66. Stop means 62a is attached by a retention means, such as bracket 62b, within hollow sleeve 62, allowing fluid flow of the liquid medication through lots 62a and 62b and then through aperture 62d of hollow sleeve 62.

Sleeve 62 accepts screw cap activating handle 68 after a user inserts capsule 66 into sleeve 62. Screw cap 68 engages projection means on capsule 66 so as to twist capsule 66 within sleeve 62 when a user applies a torque force to screw cap 68. Because the lower end tear off tab 64 of capsule 66 is prevented from twisting by the stop means 62a within sleeve 66, capsule 66 is caused to shear and rupture at its lower end when a user twists cap 68.

After capsule 66 is opened by twist off of tear off tab 64, capsule 66 is subject to squeezing compression by a capsule squeezer, such as a can activator or other crushing device known to those skilled in the art. Liquid medication within capsule 66 flows by gravity into nebulizing chamber 15 upon rupture of the lower end of capsule 66. The liquid medication is then conventionally nebulized and the user gets the therapeutic benefit of the nebulizer in a conventional manner.

FIG. 6 shows an exploded view of the second embodiment for the novel medication storage sleeve 62 projects vertically downward from the top of horizontal inhaling pipe 70 extending downwardly into the nebulizer housing 10 to a point just above the nebulizing chamber 15. A medication dose capsule 66 is an elongated substantially cylindrical container oriented vertically within sleeve 62.

Capsule 66 is user inserted and user removed respectively to and from sleeve 62. Capsule 66 is intended to be stored in sleeve 66 until used, and then removed and replaced in preparation for a next use of the nebulizer.

Capsule 66 has a lower end tear off tab 64. Sleeve 66 has lower end stop means to engage tear off tab 64 to prevent tab 64 from turning when torque is applied to capsule 66.

Sleeve 62 accepts screw cap activating handle 68 after a user inserts capsule 66 into sleeve 62. Screw cap 68 engages projection means on capsule 66 so as to twist capsule 66 within sleeve 62 when a user applies a torque force to screw cap 68. Because the lower end tear off tab 64 of capsule 66 is prevented from twisting by the stop means within sleeve 66, capsule 66 is caused to shear and rupture at its lower end when a user twists cap 68. Liquid medication within capsule 66 flows by gravity into nebulizing chamber 15 upon rupture of the lower end of capsule 66. The liquid medication is then conventionally nebulized and the user gets the therapeutic benefit of the nebulizer in a conventional manner.

FIG. 7 shows a detailed perspective of the second embodiment of the present invention. A user applies torque to screw cap 68 which in turn applies torque to medication capsule 66 seated within storage sleeve 62. Stop means 62*c* engages tear off tab 64 so that applied torque causes rupture of capsule 66, allowing its contents to flow by gravity into conventional nebulizer chamber 15.

FIG. 8 shows the third embodiment, having a vertical storage sleeve 62 for a capsule 66 of liquid medication, where the capsule 66 is seated with its tear-off tab 64 in close proximity to the conventional nebulizing chamber within the housing of the conventional nebulizer.

FIGS. 9, 10 and 11 show a vertical storage sleeve 62 of the third embodiment for the capsule 66 of liquid medication, showing a lever 69 actuating lever arm 69*a,* which exerts pressure against lever arm paddle 69*b* against capsule 66, thereby moving the capsule 66 laterally, while the tear-off portion 64 of the capsule is seated and immobilized within stop means 62*c,* so that lateral pushing of the capsule 66 causes a tear of the capsule 66 at the tear-off portion 64 and fluid flow through slots 62*a* and 62*b* adjacent to stop means 62*c,* through aperture 62*d* and into the fluid reservoir portion 15 of the nebulizer.

FIGS. 12-16 show a fourth alternate embodiment for a knob cam assembly for bursting the tear off tab 64 from capsule 66. As shown in FIG. 12, capsule 66 is inserted through a port in knob activator 168 between capsule pincher blades 180*a* and 180*b,* down to restraining stop means 162*c,* adjacent to one or more mist ports 162*a* and/or 162*b,* etc., which, after bursting of the seal between capsule 66 and tear off tab 68, medication is misted within nebulizer 14 upward to inhaling pipe 70 and mouthpiece 30. Ports 162*a* and/or 162*b,* as well as restraining stop means 162*c* are down stream of inhaling pipe 70, between nebulizer 14 and inhaling pipe 70.

Rotation of knob activator 168 causes twisting of capsule 66 between capsule pincher blades 180*a* and 180*b,* and thence against cam contact protrusion elements 192*a* and 192*b* of cam assembly 190, which rotates in unison with rotation of knob activator 168, while restraining stop means holds tear off tab 64 of capsule 66 during rotation of capsule 66 within cam assembly 190.

Rotation of knob activator 168 and cam assembly 190 is limited to a preferable arc of movement, such as, for example 180 degrees, by means of reciprocating stop element 194*a* on inhalation pipe 70 being stopped by reciprocating stop element 194*b* on the adjacent bottom of cam assembly 190.

FIGS. 17-33 show alternate embodiments where the medication capsule is severed by a blade at an appropriate wide portion so that ambient air pressure is not a factor, so the capsule does not need to be opened and crushed to insure fluid flow through the narrow discharge end of the capsule, as shown in FIGS. 13-16.

FIG. 17 shows the major components of a fifth embodiment of a nebulizer assembly 200 of the present invention, where the medication capsule 300 is opened by being severed with a cutting blade 270. Nebulizer assembly 200 has a vertical storage chamber 210 for containing medication dosage capsule 300 in a ready position for use by pressing on finger grip 280 of blade plunger assembly 260 urging flat blade plunger 265 within hollow flat blade plunger guide 250.

Cutting blade 270 with sharpened angled leading edge is shown in the top view of blade plunger assembly 260 in FIG. 18. Note plunger flow aperture 275 which provides an unobstructed flow region for medication to flow out of capsule 300 after it is cut. Fixed finger grip 255 provides a convenient surface for a compression action using thumb and fingers of one hand to perform the cutting motion. Note that after capsule 300 is inserted into chamber 210 in ready storage for the next asthma episode, cap 290 is used to seal the large opening 210*a* at the top of chamber 210. Cap 290 keeps capsule 300 from jumping out of after being sliced and cut. Note that after cutting, medicine will flow down into conventional nebulizing chamber 240 wherein it is broken up into fine droplets by action of compressed air being fed in from the bottom. Inhalation tube 220 with mouthpiece 230 complete the major portions of nebulizer 200.

FIGS. 19 through 22 are crossectional detail views of the progression of the cutting operation of medication dosage capsule 300 at its necked down distal end 300*a.*

In FIG. 19, blade 270 is spaced away from capsule 300; this is the normal storage position.

FIG. 20 shows blade 270 approaching the side of capsule 300 to be severed.

In FIGS. 21, blade 270 is in first contact with the side of capsule 300.

FIG. 22 shows the situation just after capsule 300 is cut with medication flowing out through plunger flow aperture 275 and from severed end 300*a.*

FIG. 23 shows the entire nebulizer system including air compressor housing 310 which is connected to nebulizer 240 via compressed air tubing 330. Also shown is fixed finger grip 555 attached to hollow plunger guide 550 for slidable insertion of blade assembly 560, shown in FIG. 24. Fixed finger grip 555 provides a convenient surface for a compression action using the fingers and hand to perform the cutting motion.

FIGS. 24-28 show the major components of the sixth alternate embodiment of a nebulizer assembly 500 of the present invention, where the medication capsule 600 is opened by being severed with a cutting blade 570 (see FIG. 24). As shown in FIGS. 26-28, the nebulizer assembly has a vertical storage chamber 510 for containing medication dosage capsule 600 in a ready position for use by pressing on hand grip 580 of blade plunger assembly 560, urging flat blade plunger 565 within hollow pocket 551 of flat blade plunger guide 550, as shown in FIG. 23.

As shown in FIG. 24, cutting blade 570 with sharpened angled leading edge (approximately 25-65 degrees, preferably 45 degrees) is shown in the perspective view of blade plunger assembly 560. FIG. 24 also shows rigid or slightly flexible follower paddle 572 with adjacent fluid flow opening 573. Follower paddle 572 pushes severed distal portion 600a out of the way as shown in FIG. 28, in preloadable chamber medication capsule storage region 510, which is located above upper platform 710, which, in turn, is located above fluid transport chamber 511. Fluid transport chamber 511 is preferably acute tunnel-shaped in configuration, for optional fluid flow of fluid, past inhalation tube 220, directly into conventional nebulizing chamber 240.

As shown in FIG. 24A, in order to assure the correct orientation of blade plunger guide 550 of blade plunger assembly 560, when inserted into hollow pocket 551 thereof, blade plunger 565 has linear tongue 552 insertable within linear groove 553 of an inside wall of blade plunger guide 550.

FIGS. 24B, 24C and 24D show another embodiment for an orientation sub-assembly for the blade plunger assembly 560. Blade plunger 565 includes a misorientation stop protrusion button 552a, which is slidably insertable within linear groove 553a within an inner top surface of blade plunger guide 550 when blade plunger 565 is correctly oriented for insertion within blade plunger assembly 550. External misorientation stop 552b is provided extending axially outward from a bottom portion of blade plunger assembly 550, to contact misorientation stop protrusion button 552a if blade plunger 565 is not correctly positioned for insertion.

FIG. 24C is a close-up front elevational view of the plunger portion thereof;

FIG. 24D is a top plan view of the plunger guide of the orientation sub-assembly of FIG. 24B;

FIG. 25 shows a detail of follower paddle 572 showing its sloping upper surface, preferably the leading edge of paddle follower 572 is flat to facilitate positive contact with severed capsule portion 600a. The paddle follower 572 is used to separate the cut capsule 600, 600a to insure that all liquid is able to drain into conventional nebulizer misting chamber 240. Follower paddle 572 is significantly smaller in area than surrounding opening 573 behind blade 570, to enhance fluid flow therethrough when pushing severed distal portion 600a out of the way. The rounded neck of follower paddle 572, as indicated by the curvature arrow, is preferably smaller in width than a crossectional area of cut capsule 600.

FIGS. 26 through 28 are crossectional detail views of the sixth embodiment, showing the progression of the cutting operation of medication dosage capsule 600 at its distal end 600a, and the pushing of severed distal portion 600a out of the way above screen 576.

In FIGS. 26 and 26A, blade 570 is spaced away from capsule 600; this is the normal storage position. Capsule 600 is preloaded to rest against capsule stabilizer block 554, which facilitates clean slicing of capsule 600. Capsule stabilizer block 554 is located above capsule base holder 710. Additionally sloping capsule guide 554a is provided juxtaposed on an opposite side of vertical storage chamber 510 so capsule 600 does not lodge by mistake into one of the peripheral holes 730 in platform 710, but rather is correctly guided and nested into central hole 720. Sloping capsule guide 554a also assists in sliding the severed capsule 600 out of the way.

In FIG. 27, blade 570 has cut through capsule 600.

FIG. 28 shows the situation just after capsule 600 is cut with medication flowing around follower paddle 522, out through plunger flow aperture 573 behind blade 570 and through discharge tube 575. Follower paddle 572 pushes severed distal portion 600a out of the way, within chamber medication capsule storage region 510. To insure separation of the cut portions of medication capsule 600 by the leading edge of follower paddle 572, the rounded top surface is angled downward so that the contact region of follower paddle 572 with cut end 600a is below the level of blade 570.

FIGS. 29-33 show the seventh embodiment of nebulizer with improved medication capsule holding features for easier cutting action.

FIG. 29 also shows an alternate design for medication capsule 700 which is wider and flatter, for example, than capsule 600 with a pointed top end 705. A modified base holder 710 has a central hole 720 with extending slots 722 which can accept a wide range of capsule designs. A capsule type 600 is held with the bottom end partially within hole 720, while a capsule of type 700 is held above hole 720 with flat end engaged within radially extending slots 722 as shown in the detail of FIG. 29. Since capsules 600 or 700 are soft in their midsection, blade cuts thereof should be close to a bottom portion thereof, so that a clean cut occurs to insure maximum emptying of fluid contents therefrom. However, the blade cut must be through the hollow fluid filled portion, not through the solid tear-off portion of capsule 600 or 700.

Other features which enhance the holding action are housed within storage chamber cap 590 as shown in FIG. 30. These include coil spring 750 which is used to press down on the top end of either style of medication capsule. Fixed spring retainer 740 engages the top distal end of coil spring 750 and retains it in a fixed position at the inside top of cap 590. Bottom collar 760 engages the bottom end of coil spring 750 and slides freely (as a piston) on the inside surface of cap 590. Attached to collar 760 is a conical top medication holder 770 which will center either the flat top and bottom ends of capsule 600 or the pointed top end 705 or flat bottom end 706 of capsule 700.

Figure 32:
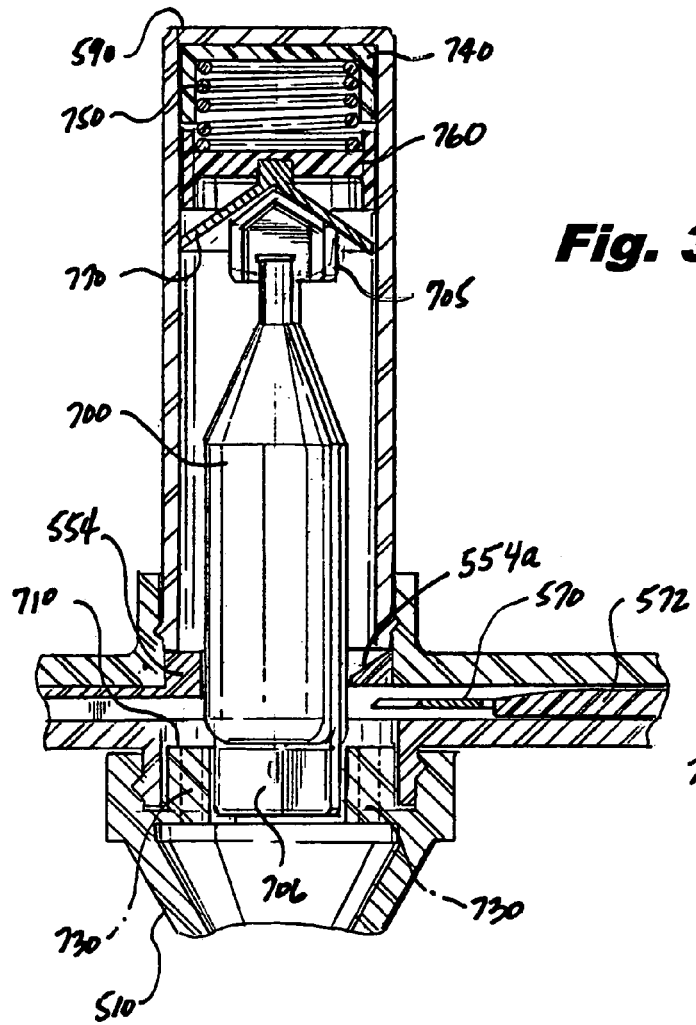
Figure 33:
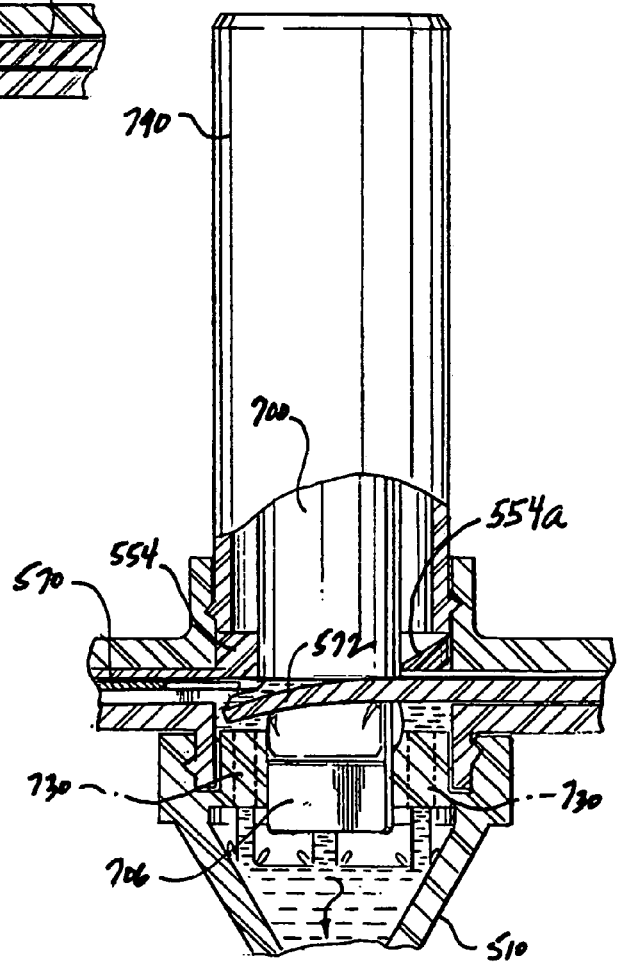

FIG. 32 shows the inner alignment of the components of the storage chamber. Note that spring 750 is compressed by the presence of either capsule 700 (as shown) or 600. This is a view just prior to blade 570 approaching the side of capsule 700. FIG. 33 is a snapshot view just after cutting of medication capsule 600 showing medication flowing through central hole 720 and peripheral holes 730 into the chamber below.

FIGS. 34-37 show an eighth alternate embodiment for a fully integrated system for turning on compressor motor 410 of compressor 420.

FIGS. 34-36 show integrated air compressor housing 311 connected to nebulizer 200 via compressed air tubing 330. Also shown is plunger switch 360 centrally mounted on fixed finger grip 555 and attached to compressor housing 311 via cable 365. Switch 360 is preferably a 2 Button "rocker" switch left in "OFF" for stand by to use. Optionally, it can be a magnetic switch or other automated switch. Switch 360 is activated by movement of plunger hand grip 580 against "ON" contact button 370, which is mounted on a lower portion of grip 555. Switch 360 is a waterproof switch, such as, for example, a 2-wire, maintained contact 2 Button "rocker", such as provided by Control Products, Inc. in their K5000 Series industrial waterproof switches. "OFF" switch button 370a, located below "ON" switch button 370, turns off the circuit and puts the system back to "stand by" status. It can be re-energized by pressing manual compressor switch button 340 or by re-activating plunger assembly 560, causing contact of hand grip 580 against "ON" switch button 370 of switch 360 located on fixed finger grip 555.

FIG. 35 shows these two parts, fixed hand grip 580 and "ON" switch button 370 contacting each other upon actuation. Preferably, optional resilient contact button bumper 580a insures contact between fixed hand grip 580 and "ON" button 370. In operation, nebulizer 200 would be stored with medication dosage capsule 300, 600 or 700 stored in ready orientation in chamber 210. Compressor wall plug 320 would be normally energized in an AC power source outlet. Manual override button 340, only necessary in case of failure of switch 360, or any part of the circuit would be in the "OFF" position. In a usage situation (possibly in the throes of an asthma attack), the user need only press plunger hand grip 580 toward fixed finger grip 555, activating "ON" button 370 of switch 360, thereby cutting capsule 300 emptying medication into conventional nebulizing chamber 240 and then inhaling through mouthpiece 230. The action of cutting capsule 300 simultaneously switches on the compressor without use of manual switch 340 on compressor housing 311. The system is a fault tolerant system, wherein if the circuit fails, override button 340 will complete the circuit directly to motor 410, bypassing contacts 395 of relay 380 thereby operating regardless of multiple failures of switch 360, cable 365 or relay 380.

A locator light emitting indicator outlet 313 is optional to put a "night light" 315 therein. Outlet 313 is always "ON". Holder 314 has a slot for engaging the end of flat blade plunger guide 250 as well as a partial round cutout to accommodate the curvature of cap 290, for easy storage of nebulizer opening assembly and inhaler therein.

Figure 37:
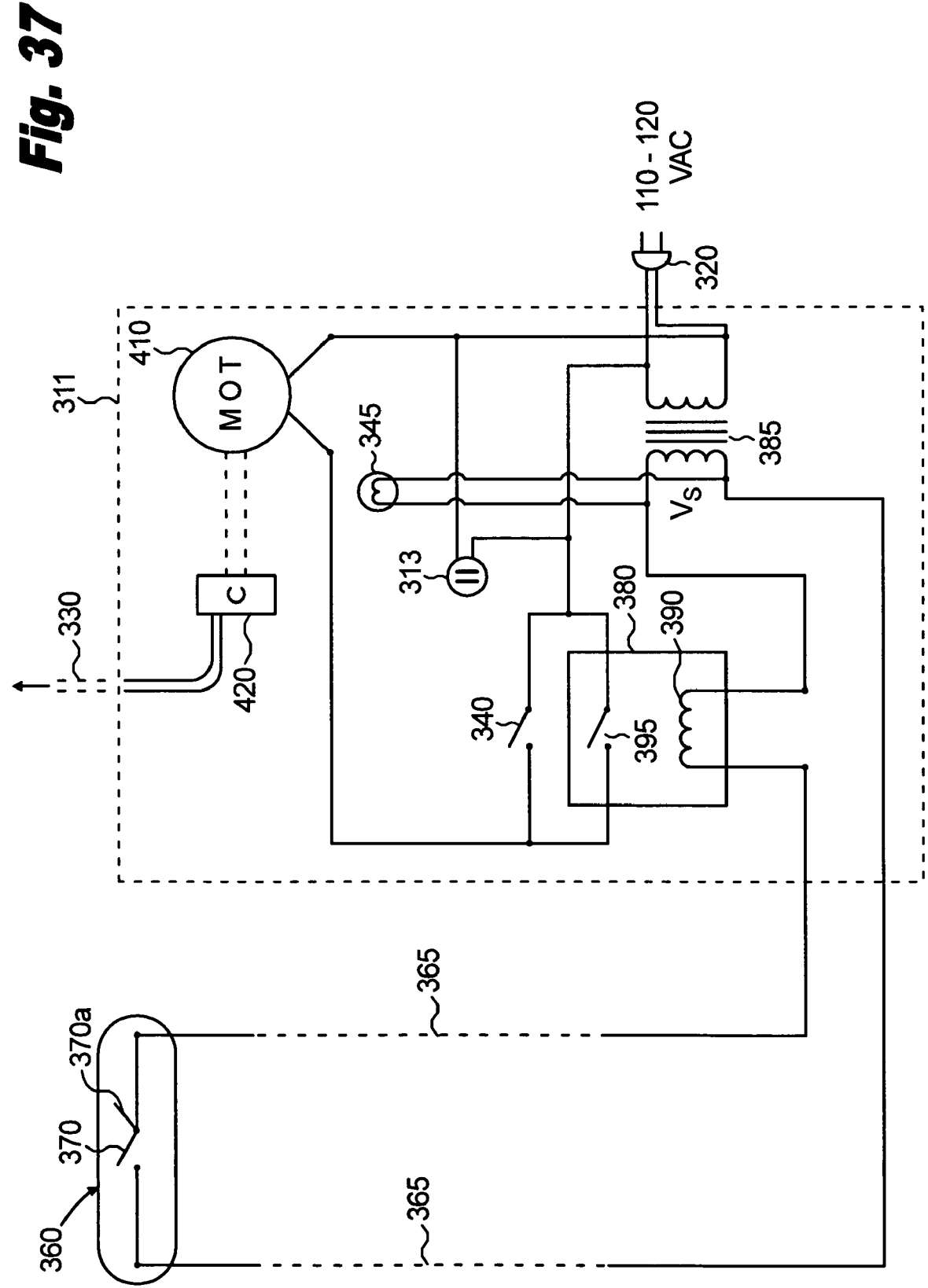

The schematic diagram of FIG. 37 explains the operation and shows the physical location of major components shown in FIGS. 34-36 since dashed line 311, in the schematic diagram of FIG. 37, shows the boundary of compressor housing 311. Transformer 385 supplies a low voltage Vs (typically a safe 12 or 24 volts) to operate relay 380 and indicator lamp 345 which is always on as an indicator that transformer 385 is operating on stand by energize relay coil 390 when switch 360 is on and the circuit is complete. Note that actuation of switch 360 by action of ON button 370 would provide voltage Vs to relay coil 390 thereby causing normally open relay contacts 395 to close thereby energizing compressor motor 410. In the unlikely event that operation is not initiated by attempted actuation of switch 360, manual switch 340 on compressor housing 311 can be used to initiate operation since it is wired directly to motor 410. Note that transformer 385 is continuously energized as long as plug 320 is plugged-in so that the entire nebulizer system is in a quick-ready mode of operation at all times. Compressor 420 is driven by motor 410 to supply air pressure to nebulizing chamber 240 to atomize medication in a mist to the patient.

Figure 38:
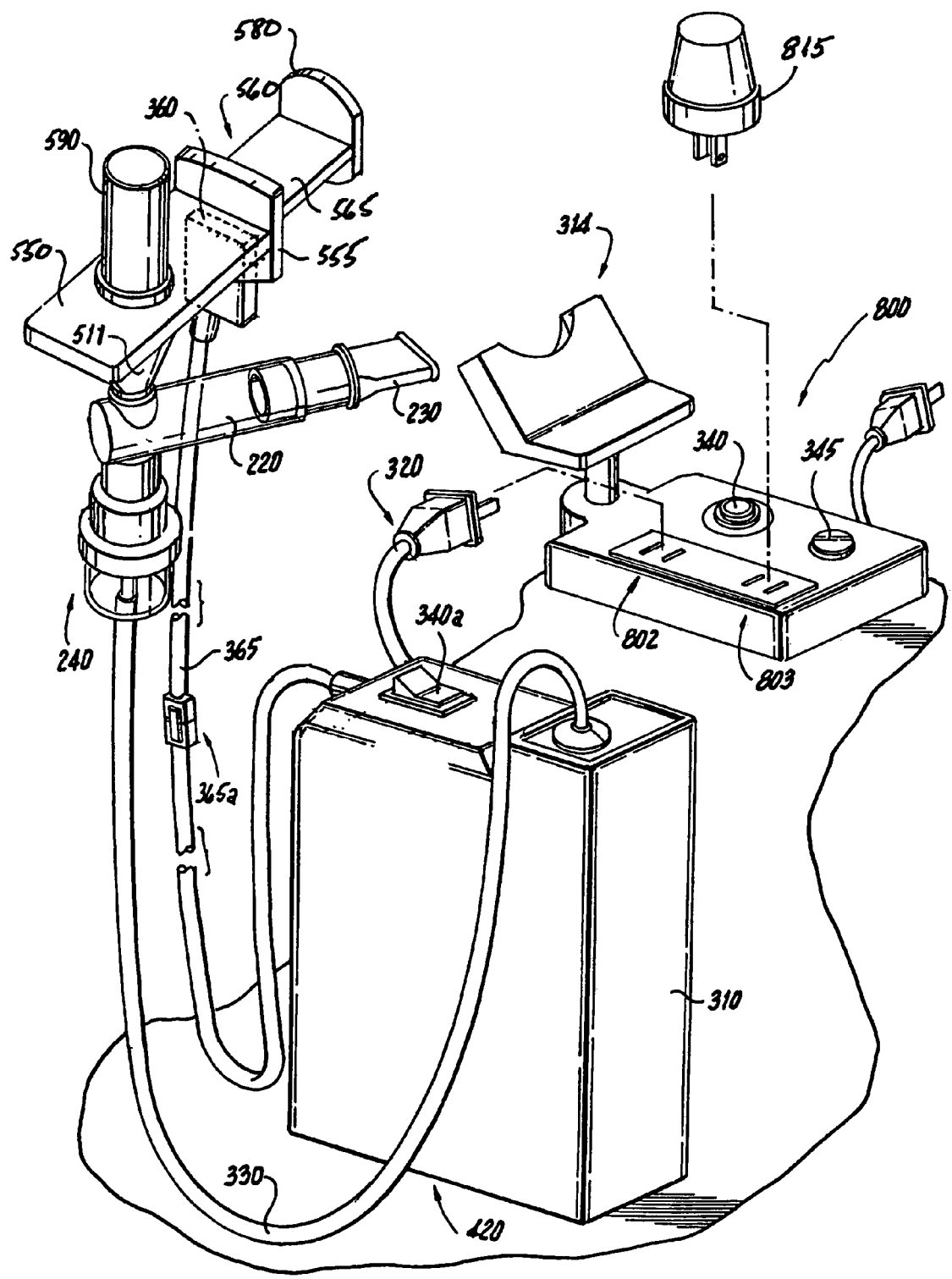

FIG. 38 shows a ninth embodiment for an auxiliary plug-in starting box 800 for automatically starting the misting compressor motor 410 of a conventional compressor housing 310 of the nebulizer inhaler. This embodiment is a retrofit for a conventional compressor subassembly.

Figure 39:
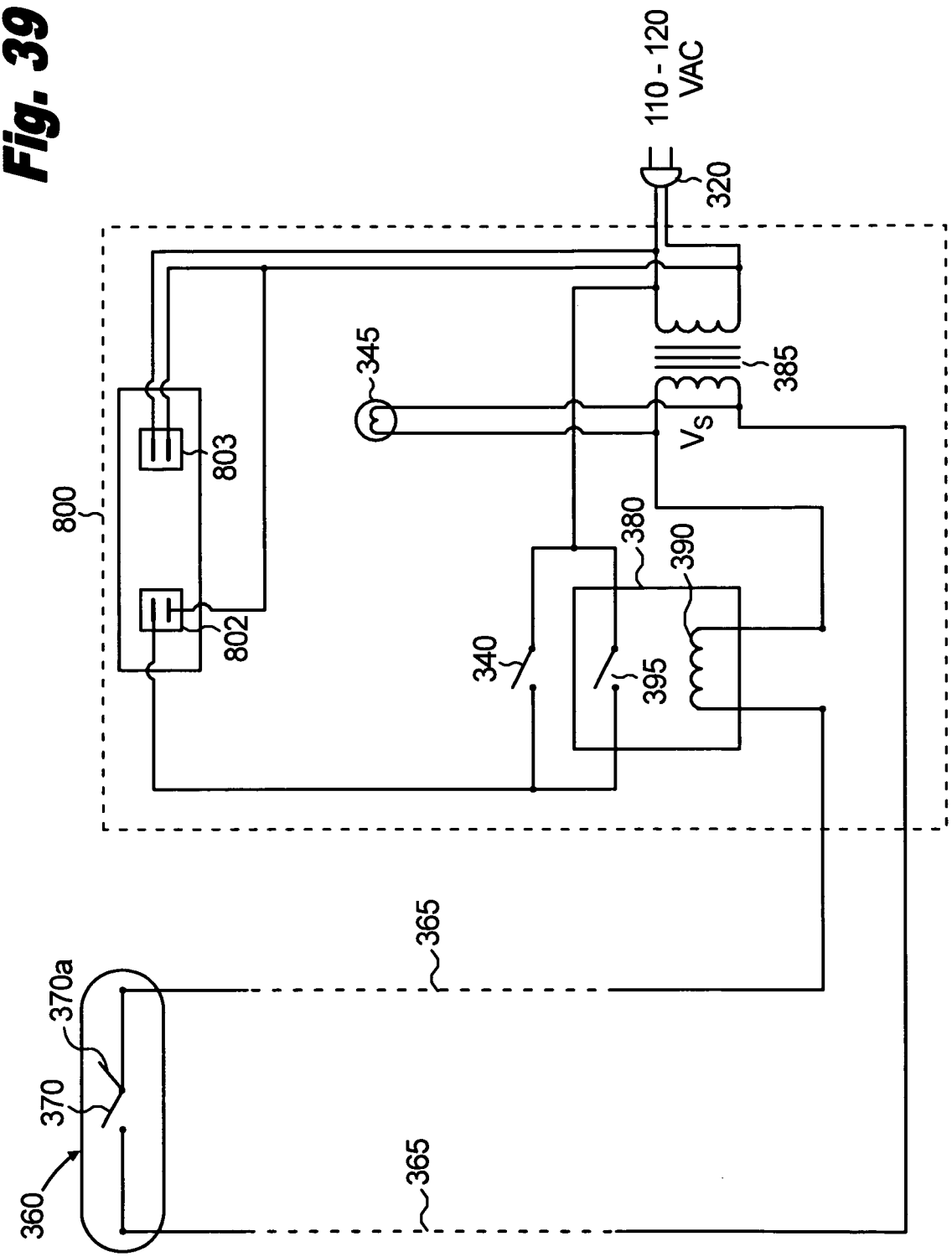

FIG. 39 is an electrical schematic diagram thereof. One outlet 802 is provided for inserting the plug 320 from the nebulizer compressor motor 410. The other outlet 803 is for a user insertable plug for a night light 815, to provide visual access in the dark. The backup emergency press button 340a will start the nebulizer compressor motor 410 of conventional compressor housing 310 of FIG. 38 if the plunger 560 does not work. Green indicator light 345 indicates that the transformer 385 for the compressor is "ON." Nebulizer holder 314 is provided to hold plunger guide 550 therein. Plunger assembly 550 also includes switch 360 with "ON" switch button 370 and "OFF" button 370a such as is shown in FIGS. 35 and 36 and applicable herein. Switch 360 is activated upon contact of button 370 by hand grip 580. Nebulizer plug 320 is energized when either switch 360 or switch 340a is closed. The system is a fault tolerant system—if the circuit fails, compressor manual switch 340a is available to activate.

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention, without departing the scope of the invention, as noted in the appended Claims.

I claim:

1. A semi-automatic emergency medication dose nebulizer comprising:
    a vertically extending housing having a nebulizer chamber to receive liquid containing medication;
    an opening in a bottom of said housing to receive compressed air from a compressor for nebulizing said medication;
    a horizontally extending breather above said nebulizer housing joined to said housing through a connecting tube extending up vertically from said housing for receiving nebulized medication;
    said breather having a mouthpiece for use by a patient to receive said nebulized medication;
    an apparatus for recharging said nebulizing chamber with medication mounted on said breather;
    said apparatus comprising a recharging tube containing a capsule storage chamber aligned with said connecting tube for receiving a vertically oriented medication dosage capsule containing a liquid medication; and
    means comprising a horizontally extending cutting blade for completely severing said vertically oriented liquid medication dosage capsule by slicing through a side of said capsule causing removal and relocation of a lower portion of said capsule; said blade having a follower paddle mounted behind said horizontally oriented blade to push a severed portion of said vertically oriented capsule out of the line of flow of said medication, allowing liquid medication to flow downward when released from said capsule, to flow under the influence of gravity into said nebulizing chamber.

2. The semi-automatic emergency medication dose nebulizer of claim 1 in which said severing means comprises a cutting assembly mounted on said recharging tube.

3. The semi-automatic emergency medication dose nebulizer of claim 2 in which said cutting assembly comprises a plunger guide, a plunger slidable in said plunger guide, and a flat blade mounted on a leading edge of said plunger to sever said capsule when said plunger is advanced into said recharging tube.

4. The semi-automatic emergency medication dose nebulizer of claim 3 in which said plunger has a plunger flow aperture behind said flat blade to allow flow of medication behind said blade after said capsule is severed by said blade.

5. The semi-automatic emergency medication dose nebulizer of claim 4 in which said plunger guide and plunger have fixed grips to permit single hand operation to release medication into said medication chamber.

6. The semi-automatic emergency medication dose nebulizer of claim 5 in which said blade has an angled cutting edge at a diagonal angle of about 45 degrees from a side of said plunger.

7. The semi-automatic emergency medication dose nebulizer of claim 6 in which said recharging tube has a top opening to receive said capsule, said top opening having a removable cap for covering said top opening when said capsule is within said recharging tube.

8. The semi-automatic emergency medication dose nebulizer of claim 7 in which said follower paddle has a rounded top surface angled downwardly to that a contact region of follower paddle is below said cutting blade.

9. The semi-automatic emergency medication dose nebulizer of claim 8 in which said storage chamber includes a capsule loading region including a capsule support platform having a capsule positioning hole positioning the capsule at a positive location for appropriate predetermined location of contact of said cutting blade against said capsule.

10. The semi-automatic emergency medication dose nebulizer of claim 9 further comprising a capsule stabilizing block provided on one side of said storage chamber and a capsule guide provided juxtaposed on an opposite side of said storage chamber, to prevent lodging of said capsule into a fluid drip hole, and to facilitate nesting of said capsule into a capsule positioning hole of a capsule nesting platform.

11. The semi-automatic emergency medication dose nebulizer of claim 9 having a coil spring mounted in said cap to press down on said capsule within said storage chamber.

* * * * *